US012570763B2

(12) United States Patent
Chan et al.

(10) Patent No.: US 12,570,763 B2
(45) Date of Patent: Mar. 10, 2026

(54) AEROSOLIZED MUCUS-TETHERING NANOBODIES TO PROTECT AGAINST VIRAL AND MICROBIAL CONTAMINATION IN CLOSED AND SEMI-ENCLOSED SPACES

(71) Applicant: The Board of Trustees of the Leland Stanford Junior University, Stanford, CA (US)

(72) Inventors: Charles K. F. Chan, Redwood City, CA (US); Liming Zhao, Stanford, CA (US); Yunxiao Zhang, La Jolla, CA (US); Yuting Wang, Stanford, CA (US); Andrew Lee, Stanford, CA (US); Michael T. Longaker, Atherton, CA (US); Holly Steininger, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 617 days.

(21) Appl. No.: 17/927,600

(22) PCT Filed: May 27, 2021

(86) PCT No.: PCT/US2021/034492
§ 371 (c)(1),
(2) Date: Nov. 23, 2022

(87) PCT Pub. No.: WO2021/243005
PCT Pub. Date: Dec. 2, 2021

(65) Prior Publication Data
US 2023/0218777 A1    Jul. 13, 2023

Related U.S. Application Data

(60) Provisional application No. 63/031,443, filed on May 28, 2020.

(51) Int. Cl.
C07K 16/30        (2006.01)
A61K 9/00         (2006.01)
(Continued)

(52) U.S. Cl.
CPC ........ *C07K 16/3092* (2013.01); *A61K 9/0043* (2013.01); *A61K 47/6841* (2017.08);
(Continued)

(58) Field of Classification Search
CPC ........................ C07K 16/3092; A61K 47/6841
See application file for complete search history.

(56) References Cited

U.S. PATENT DOCUMENTS

2013/0137856 A1    5/2013    Steyaert et al.

FOREIGN PATENT DOCUMENTS

WO        WO 2013135655        9/2013
WO        WO 2018208877        11/2018

OTHER PUBLICATIONS

Li Y, Zhou C, Li J, Liu J, Lin L, Li L, et al. (2018) Single domain based bispecific antibody, Muc1-Bi-1, and its humanized form, Muc1-Bi-2, induce potent cancer cell killing in muc1 positive tumor cells. PLoS ONE 13(1): e0191024. https://doi.org/10.1371/journal.pone.0191024 (Year: 2018).*

* cited by examiner

*Primary Examiner* — Sue X Liu
(74) *Attorney, Agent, or Firm* — Pamela J. Sherwood; Andrew J. Guzman; Bozicevic, Field & Francis LLP

(57)        ABSTRACT

Provided are innovative compositions for tethering blocking an inactivating of airborne respiratory infectious viruses. The compositions comprise bispecific proteins with two different antigen binding regions (ABR), which are typically configured as immunoglobulin "single variable domains" (ISV). A first ISV binds to a surface protein found on an (Continued)

airborne infectious virus. A second ISV binds to a mucin protein, e.g. a mucin protein present on ocular, nasopharyngeal, tracheal and/or oral surfaces of a mammal. The two ISV are joined by a polypeptide linker.

20 Claims, 7 Drawing Sheets

Specification includes a Sequence Listing.

(51) Int. Cl.

| | | |
|---|---|---|
| *A61K 47/68* | (2017.01) | |
| *A61P 31/14* | (2006.01) | |
| *C07K 16/102* | (2026.01) | |
| *C07K 16/104* | (2026.01) | |

(52) U.S. Cl.
CPC ...... *A61K 47/6843* (2017.08); *A61K 47/6889* (2017.08); *A61P 31/14* (2018.01); *C07K 16/102* (2026.01); *C07K 16/104* (2026.01)

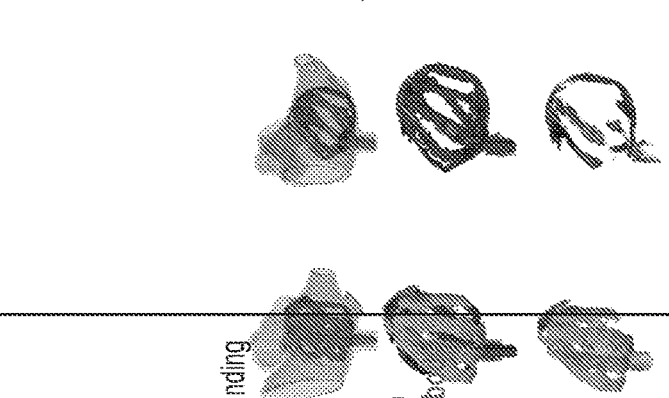

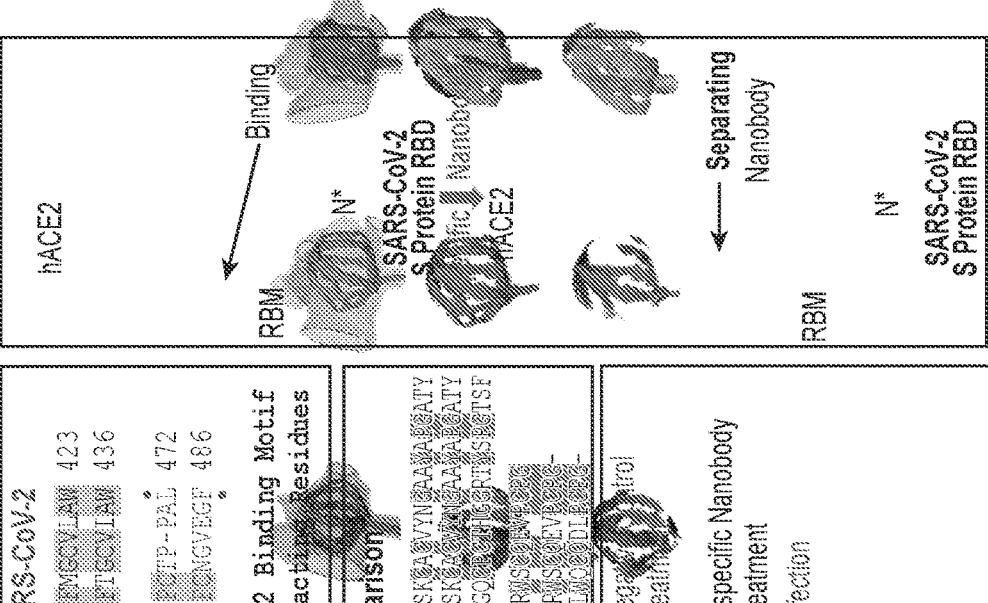

Spike Protein Receptor-Binding Domain (RBD) Analysis: SARS-CoV & SARS-CoV-2

```
SARS-CoV   RBD 374  ...                                      423
SARS-CoV-2 RBD 387  ...                                      436

SARS-CoV   RBD 424  ...                                      472
SARS-CoV-2 RBD 437  ...                                      486

SARS-CoV   RBD 473  ...                                      502
SARS-CoV-2 RBD 487  ...                                      516
```

RED  ACE2 Binding Motif
**  Contact Residues hACE2 — Binding — RBM — N* — SARS-CoV-2 S Protein RBD — hACE2 — Separating Nanobody — RBM — N* — SARS-CoV-2 S Protein RBD

Primary Gel-Forming Mucin Analysis

| Mucosa | Gel-Forming Mucins | | |
|---|---|---|---|
| Ocular Mucosa | MUC5AC | | |
| Oral Mucosa | MUC5AC | MUC5B | |
| Nasopharyngeal Mucosa | MUC5AC | MUC5B | |
| Tracheal Mucosa | MUC5AC | MUC5B | |

Sequence Comparison

```
MUC5AC Antigen
MUC5AC Segment
MUC5B Segment

MUC5AC Antigen
MUC5AC Segment
MUC5B Segment
```

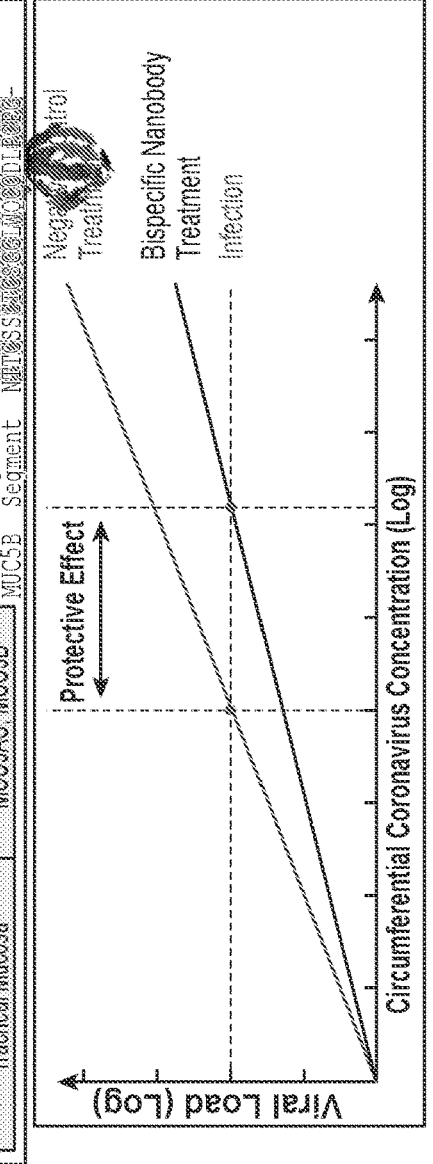

Protective Effect

Negative Control Treatment

Bispecific Nanobody Treatment

Infection

Viral Load (Log)

Circumferential Coronavirus Concentration (Log)

FIG. 2

SEQUENCE LISTING

<160> NUMBER OF SEQ ID NOS: 102

<210> SEQ ID NO 1
<211> LENGTH: 223
<212> TYPE: PRT
<213> ORGANISM: Severe acute respiratory syndrome coronavirus

<400> SEQUENCE: 1

```
Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
            35                  40                  45

Val Leu Tyr Asn Ser Ala Ser Phe Ser Thr Phe Lys Cys Tyr Gly Val
        50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
            115                 120                 125

Gly Asn Tyr Asn Tyr Leu Tyr Arg Leu Phe Arg Lys Ser Asn Leu Lys
        130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
                180                 185                 190

Val Val Leu Ser Phe Glu Leu Leu His Ala Pro Ala Thr Val Cys Gly
            195                 200                 205

Pro Lys Lys Ser Thr Asn Leu Val Lys Asn Lys Cys Val Asn Phe
        210                 215                 220
```

<210> SEQ ID NO 2
<211> LENGTH: 222
<212> TYPE: PRT
<213> ORGANISM: Severe acute respiratory syndrome coronavirus -continued

```
<400> SEQUENCE: 2

Arg Val Val Pro Ser Gly Asp Val Val Arg Phe Pro Asn Ile Thr Asn
1               5                   10                  15

Leu Cys Pro Phe Gly Glu Val Phe Asn Ala Thr Lys Phe Pro Ser Val
            20                  25                  30

Tyr Ala Trp Glu Arg Lys Lys Ile Ser Asn Cys Val Ala Asp Tyr Ser
        35                  40                  45

Val Leu Tyr Asn Ser Thr Phe Phe Ser Thr Phe Lys Cys Tyr Gly Val
    50                  55                  60

Ser Ala Thr Lys Leu Asn Asp Leu Cys Phe Ser Asn Val Tyr Ala Asp
65                  70                  75                  80

Ser Phe Val Val Lys Gly Asp Val Arg Gln Ile Ala Pro Gly Gln
                85                  90                  95

Thr Gly Val Ile Ala Asp Tyr Asn Tyr Lys Leu Pro Asp Asp Phe Met
            100                 105                 110

Gly Cys Val Leu Ala Trp Asn Thr Arg Asn Ile Asp Ala Thr Ser Thr
            115                 120                 125

Gly Asn Tyr Asn Tyr Lys Tyr Arg Tyr Leu Arg His Gly Lys Leu Arg
    130                 135                 140

Pro Phe Glu Arg Asp Ile Ser Asn Val Pro Phe Ser Pro Asp Gly Lys
145                 150                 155                 160

Pro Cys Thr Pro Pro Ala Leu Asn Cys Tyr Trp Pro Leu Asn Asp Tyr
            165                 170                 175

Gly Phe Tyr Thr Thr Thr Gly Ile Gly Tyr Gln Pro Tyr Arg Val Val
            180                 185                 190

Val Leu Ser Phe Glu Leu Leu Asn Ala Pro Ala Thr Val Cys Gly Pro
        195                 200                 205

Lys Leu Ser Thr Asp Leu Ile Lys Asn Gln Cys Val Asn Phe
    210                 215                 220

<210> SEQ ID NO 3
<211> LENGTH: 240
<212> TYPE: PRT
<213> ORGANISM: Middle East respiratory syndrome coronavirus

<400> SEQUENCE: 3

Glu Ala Lys Pro Ser Gly Ser Val Val Glu Gln Ala Glu Gly Val Glu
1               5                   10                  15

Cys Asp Phe Ser Pro Leu Leu Ser Gly Thr Pro Pro Gln Val Tyr Asn
            20                  25                  30

Phe Lys Arg Leu Val Phe Thr Asn Cys Asn Tyr Asn Leu Thr Lys Leu
        35                  40                  45

Leu Ser Leu Phe Ser Val Asn Asp Phe Thr Cys Ser Gln Ile Ser Pro
    50                  55                  60

Ala Ala Ile Ala Ser Asn Cys Tyr Ser Ser Leu Ile Leu Asp Tyr Phe
65                  70                  75                  80

Ser Tyr Pro Leu Ser Met Lys Ser Asp Leu Ser Val Ser Ser Ala Gly
                85                  90                  95

Pro Ile Ser Gln Phe Asn Tyr Lys Gln Ser Phe Ser Asn Pro Thr Cys
            100                 105                 110

Leu Ile Leu Ala Thr Val Pro His Asn Leu Thr Thr Ile Thr Lys Pro
        115                 120                 125

Leu Lys Tyr Ser Tyr Ile Asn Lys Cys Ser Arg Phe Leu Ser Asp Asp
    130                 135                 140
```

-continued

```
Arg Thr Glu Val Pro Gln Leu Val Asn Ala Asn Gln Tyr Ser Pro Cys
145                 150                 155                 160

Val Ser Ile Val Pro Ser Thr Val Trp Glu Asp Gly Asp Tyr Tyr Arg
                165                 170                 175

Lys Gln Leu Ser Pro Leu Glu Gly Gly Gly Trp Leu Val Ala Ser Gly
                180                 185                 190

Ser Thr Val Ala Met Thr Glu Gln Leu Gln Met Gly Phe Gly Ile Thr
                195                 200                 205

Val Gln Tyr Gly Thr Asp Thr Asn Ser Val Cys Pro Lys Leu Glu Phe
        210                 215                 220

Ala Asn Asp Thr Lys Ile Ala Ser Gln Leu Gly Asn Cys Val Glu Tyr
225                 230                 235                 240
```

<210> SEQ ID NO 4
<211> LENGTH: 511
<212> TYPE: PRT
<213> ORGANISM: Influenza A virus

<400> SEQUENCE: 4

```
Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
                20                  25                  30

Leu Glu Asp Ser His Asn Gly Lys Leu Cys Arg Leu Lys Gly Ile Ala
        35                  40                  45

Pro Leu Gln Leu Gly Lys Cys Asn Ile Ala Gly Trp Leu Leu Gly Asn
    50                  55                  60

Pro Glu Cys Asp Pro Leu Leu Pro Val Arg Ser Trp Ser Tyr Ile Val
65                  70                  75                  80

Glu Thr Pro Asn Ser Glu Asn Gly Ile Cys Tyr Pro Gly Asp Phe Ile
                85                  90                  95

Asp Tyr Glu Glu Leu Arg Glu Gln Leu Ser Ser Val Ser Ser Phe Glu
                100                 105                 110

Arg Phe Glu Ile Phe Pro Lys Glu Ser Ser Trp Pro Asn His Asn Thr
            115                 120                 125

Asn Gly Val Thr Ala Ala Cys Ser His Glu Gly Lys Ser Ser Phe Tyr
        130                 135                 140

Arg Asn Leu Leu Trp Leu Thr Glu Lys Glu Gly Ser Tyr Pro Lys Leu
145                 150                 155                 160

Lys Asn Ser Tyr Val Asn Lys Lys Gly Lys Glu Val Leu Val Leu Trp
                165                 170                 175

Gly Ile His His Pro Pro Asn Ser Lys Glu Gln Gln Asn Leu Tyr Gln
                180                 185                 190

Asn Glu Asn Ala Tyr Val Ser Val Val Thr Ser Asn Tyr Asn Arg Arg
                195                 200                 205

Phe Thr Pro Glu Ile Ala Glu Arg Pro Lys Val Arg Asp Gln Ala Gly
        210                 215                 220

Arg Met Asn Tyr Tyr Trp Thr Leu Leu Lys Pro Gly Asp Thr Ile Ile
225                 230                 235                 240

Phe Glu Ala Asn Gly Asn Leu Ile Ala Pro Met Tyr Ala Phe Ala Leu
                245                 250                 255

Ser Arg Gly Phe Gly Ser Gly Ile Ile Thr Ser Asn Ala Ser Met His
            260                 265                 270

Glu Cys Asn Thr Lys Cys Gln Thr Pro Leu Gly Ala Ile Asn Ser Ser
            275                 280                 285
```

```
Leu Pro Tyr Gln Asn Ile His Pro Val Thr Ile Gly Glu Cys Pro Lys
    290                 295                 300

Tyr Val Arg Ser Ala Lys Leu Arg Met Val Thr Gly Leu Arg Asn Ile
305                 310                 315                 320

Pro Ser Ile Gln Ser Arg Gly Leu Phe Gly Ala Ile Ala Gly Phe Ile
                325                 330                 335

Glu Gly Gly Trp Thr Gly Met Ile Asp Gly Trp Tyr Gly Tyr His His
            340                 345                 350

Gln Asn Glu Gln Gly Ser Gly Tyr Ala Ala Asp Gln Lys Ser Thr Gln
        355                 360                 365

Asn Ala Ile Asn Gly Ile Thr Asn Lys Val Asn Thr Val Ile Glu Lys
    370                 375                 380

Met Asn Ile Gln Phe Thr Ala Val Gly Lys Glu Phe Asn Lys Leu Glu
385                 390                 395                 400

Lys Arg Met Glu Asn Leu Asn Lys Lys Val Asp Asp Gly Phe Leu Asp
                405                 410                 415

Ile Trp Thr Tyr Asn Ala Glu Leu Leu Val Leu Leu Glu Asn Glu Arg
            420                 425                 430

Thr Leu Asp Phe His Asp Ser Asn Val Lys Asn Leu Tyr Glu Lys Val
        435                 440                 445

Lys Ser Gln Leu Lys Asn Asn Ala Lys Glu Ile Gly Asn Gly Cys Phe
    450                 455                 460

Glu Phe Tyr His Lys Cys Asp Asn Glu Cys Met Glu Ser Val Arg Asn
465                 470                 475                 480

Gly Thr Tyr Asp Tyr Pro Lys Tyr Ser Glu Glu Ser Lys Leu Asn Arg
                485                 490                 495

Glu Lys Val Asp Gly Val Lys Leu Glu Ser Met Gly Ile Tyr Gln
                500                 505                 510

<210> SEQ ID NO 5
<211> LENGTH: 515
<212> TYPE: PRT
<213> ORGANISM: Homo sapiens

<400> SEQUENCE: 5

Gln Asp Leu Pro Gly Asn Asp Asn Ser Thr Ala Thr Leu Cys Leu
1               5               10                  15

Gly His His Ala Val Pro Asn Gly Thr Leu Val Lys Thr Ile Thr Asn
            20                  25                  30

Asp Gln Ile Glu Val Thr Asn Ala Thr Glu Leu Val Gln Ser Ser Ser
        35                  40                  45

Thr Gly Lys Ile Cys Asn Asn Pro His Arg Ile Leu Asp Gly Ile Asn
    50                  55                  60

Cys Thr Leu Ile Asp Ala Leu Leu Gly Asp Pro His Cys Asp Gly Phe
65                  70                  75                  80

Gln Asn Glu Lys Trp Asp Leu Phe Val Glu Arg Ser Lys Ala Phe Ser
                85                  90                  95

Asn Cys Tyr Pro Tyr Asp Val Pro Asp Tyr Ala Ser Leu Arg Ser Leu
                100                 105                 110

Val Ala Ser Ser Gly Thr Leu Glu Phe Ile Asn Glu Gly Phe Asn Trp
            115                 120                 125

Thr Gly Val Thr Gln Asn Gly Gly Ser Ser Ala Cys Lys Arg Gly Pro
    130                 135                 140

Asp Ser Gly Phe Phe Ser Arg Leu Asn Trp Leu Tyr Lys Ser Gly Ser
```

-continued

```
145                 150                 155                 160

Thr Tyr Pro Val Gln Asn Val Thr Met Pro Asn Asn Asp Asn Ser Asp
            165                 170                 175

Lys Leu Tyr Ile Trp Gly Val His His Pro Ser Thr Asp Lys Glu Gln
            180                 185                 190

Thr Asn Leu Tyr Val Gln Ala Ser Gly Lys Val Thr Val Ser Thr Lys
            195                 200                 205

Arg Ser Gln Gln Thr Ile Ile Pro Asn Val Gly Ser Arg Pro Trp Val
    210                 215                 220

Arg Gly Leu Ser Ser Arg Ile Ser Ile Tyr Trp Thr Ile Val Lys Pro
225                 230                 235                 240

Gly Asp Ile Leu Val Ile Asn Ser Asn Gly Asn Leu Ile Ala Pro Arg
            245                 250                 255

Gly Tyr Phe Lys Met Arg Thr Gly Lys Ser Ser Ile Met Arg Ser Asp
            260                 265                 270

Ala Pro Ile Gly Thr Cys Ser Ser Glu Cys Ile Thr Pro Asn Gly Ser
            275                 280                 285

Ile Pro Asn Asp Lys Pro Phe Gln Asn Val Asn Lys Ile Thr Tyr Gly
            290                 295                 300

Ala Cys Pro Lys Tyr Val Lys Gln Asn Thr Leu Lys Leu Ala Thr Gly
305                 310                 315                 320

Met Arg Asn Val Pro Glu Lys Gln Thr Arg Gly Ile Phe Gly Ala Ile
            325                 330                 335

Ala Gly Phe Ile Glu Asn Gly Trp Glu Gly Met Ile Asp Gly Trp Tyr
            340                 345                 350

Gly Phe Arg His Gln Asn Ser Glu Gly Thr Gly Gln Ala Ala Asp Leu
            355                 360                 365

Lys Ser Thr Gln Ala Ala Ile Asp Gln Ile Asn Gly Lys Leu Asn Arg
    370                 375                 380

Val Ile Glu Lys Thr Asn Glu Lys Phe His Gln Ile Glu Lys Glu Phe
385                 390                 395                 400

Ser Glu Val Glu Gly Arg Ile Gln Asp Leu Glu Lys Tyr Val Glu Asp
            405                 410                 415

Thr Lys Ile Asp Leu Trp Ser Tyr Asn Ala Glu Leu Leu Val Ala Leu
            420                 425                 430

Glu Asn Gln His Thr Ile Asp Leu Thr Asp Ser Glu Met Asn Lys Leu
            435                 440                 445

Phe Glu Lys Thr Arg Arg Gln Leu Arg Glu Asn Ala Glu Asp Met Gly
    450                 455                 460

Asn Gly Cys Phe Lys Ile Tyr His Lys Cys Asp Asn Ala Cys Ile Gly
465                 470                 475                 480

Ser Ile Arg Asn Gly Thr Tyr Asp His Asp Val Tyr Arg Asp Glu Ala
            485                 490                 495

Leu Asn Asn Arg Phe Gln Ile Lys Gly Val Glu Leu Lys Ser Gly Tyr
            500                 505                 510

Lys Asp Trp
            515
```

<210> SEQ ID NO 6
<211> LENGTH: 92
<212> TYPE: PRT
<213> ORGANISM: Homo sapiens

<400> SEQUENCE: 6

```
Trp Thr Lys Trp Phe Asp Val Asp Phe Pro Ser Pro Gly Pro His Gly
1               5                   10                  15

Gly Asp Lys Glu Thr Tyr Asn Asn Ile Ile Arg Ser Gly Glu Lys Ile
            20                  25                  30

Cys Arg Arg Pro Glu Glu Ile Thr Arg Leu Gln Cys Arg Ala Glu Ser
        35                  40                  45

His Pro Glu Val Asn Ile Glu His Leu Gly Gln Val Val Gln Cys Ser
    50                  55                  60

Arg Glu Glu Gly Leu Val Cys Arg Asn Gln Asp Gln Gln Gly Pro Phe
65                  70                  75                  80

Lys Met Cys Leu Asn Tyr Glu Val Arg Val Leu Cys
                85                  90
```

```
<210> SEQ ID NO 7
<211> LENGTH: 91
<212> TYPE: PRT
<213> ORGANISM: Mus musculus

<400> SEQUENCE: 7

Trp Thr Lys Trp Phe Asp Thr Asp Phe Pro Val Pro Gly Pro His Gly
1               5                   10                  15

Gly Asp Leu Glu Thr Tyr Ser Asn Ile Glu Arg Ser Gly Glu Arg Leu
            20                  25                  30

Cys His Arg Glu Glu Ile Thr Gln Leu Gln Cys Arg Ala Lys Asn Tyr
        35                  40                  45

Pro Glu Arg Glu Met Glu Asp Leu Gly Gln Val Val Lys Cys Asp Pro
    50                  55                  60

Ser Val Gly Leu Val Cys Asn Asn Arg Asp Gln Gly Gly Asp Ser Gly
65                  70                  75                  80

Met Cys Leu Asn Tyr Glu Val Arg Leu Leu Cys
                85                  90
```

```
<210> SEQ ID NO 8
<211> LENGTH: 197
<212> TYPE: PRT
<213> ORGANISM: Mesocricetus auratus

<400> SEQUENCE: 8

Asn Trp Thr Asp Trp Ile Asp Gly Ser Tyr Pro Gly Pro Asp Arg Asn
1               5                   10                  15

Ser Gly Asp Phe Asp Thr Phe Ala Asn Leu Arg Ser Lys Gly Tyr Lys
            20                  25                  30

Phe Cys Glu Lys Pro Gln Asn Val Glu Cys Arg Ala Gln Phe Phe Pro
        35                  40                  45

Asn Thr Pro Leu Glu Glu Leu Gly Gln Asp Val Thr Cys Asn Arg Asp
    50                  55                  60

Glu Gly Leu Ile Cys Leu Asn Lys Asn Gln Leu Pro Pro Ile Cys Tyr
65                  70                  75                  80

Asn Tyr Glu Ile Arg Ile Glu Cys Cys Thr Ile Val Asp Thr Cys Ser
                85                  90                  95

Thr Ala Ser Thr Thr Thr His Pro Thr Ser His Glu Val Ser Thr Glu
            100                 105                 110

Thr Lys Thr Thr Trp Thr Thr Ser Ser His Ser Ser Ser Ser Lys Asp
        115                 120                 125

Thr Ser Thr Leu Ser Ala Thr Ile His Thr Arg Asn Arg Ala Thr Asp
    130                 135                 140
```

-continued

```
Ser Pro His Thr Ile Ser Thr Pro Val Thr Thr His Cys Gln Pro Gln
145                 150                 155                 160

Cys Thr Trp Thr Gln Trp Phe Asp Thr Asp Phe Pro Val Pro Gly Pro
                165                 170                 175

His Gly Gly Asp Leu Glu Asp Thr Ser Gly Met Cys Leu Asn Tyr Glu
            180                 185                 190

Val Arg Val Leu Cys
        195

<210> SEQ ID NO 9
<211> LENGTH: 89
<212> TYPE: PRT
<213> ORGANISM: Homo sapiens

<400> SEQUENCE: 9

Trp Ser Glu Trp Leu Asp Tyr Ser Tyr Pro Met Pro Gly Pro Ser Gly
1               5                   10                  15

Gly Asp Phe Asp Thr Tyr Ser Asn Ile Arg Ala Ala Gly Gly Ala Val
                20                  25                  30

Cys Glu Gln Pro Leu Gly Leu Glu Cys Arg Ala Gln Ala Gln Pro Gly
            35                  40                  45

Val Pro Leu Gly Glu Leu Gly Gln Val Val Glu Cys Ser Leu Asp Phe
        50                  55                  60

Gly Leu Val Cys Arg Asn Arg Glu Gln Val Gly Lys Phe Lys Met Cys
65                  70                  75                  80

Phe Asn Tyr Glu Ile Arg Val Phe Cys
                85

<210> SEQ ID NO 10
<211> LENGTH: 89
<212> TYPE: PRT
<213> ORGANISM: Homo Sapiens

<400> SEQUENCE: 10

Trp Thr Glu Trp Phe Asp Ala Asp Tyr Pro Asn Pro Gly Pro Arg Gly
1               5                   10                  15

Gly Asp Phe Glu Val Tyr Ala Val Phe Arg Glu Val Gly Tyr Ile Phe
                20                  25                  30

Cys Asp Gln Pro Lys Asp Ile Glu Cys Arg Ser Glu Lys Glu Pro Asp
            35                  40                  45

Arg Pro Leu Glu Thr Leu Glu Gln Val Val Gln Cys Asp Val Arg Phe
        50                  55                  60

Gly Leu Ile Cys Lys Asn Ile Asn Gln Ser Gly Pro Leu Gln Tyr Cys
65                  70                  75                  80

Asp Asn Tyr His Val Arg Leu Leu Cys
                85

<210> SEQ ID NO 11
<211> LENGTH: 126
<212> TYPE: PRT
<213> ORGANISM: Homo sapiens

<400> SEQUENCE: 11

Gln Val Gln Leu Gln Glu Ser Gly Gly Gly Leu Val Gln Ala Gly Gly
1               5                   10                  15

Ser Leu Arg Leu Ser Cys Ala Ala Ser Gly Thr Ile Phe Gln Val Gly
                20                  25                  30

Ser Met Gly Trp Tyr Arg Gln Ala Pro Gly Lys Glu Arg Glu Phe Val
```

-continued

```
          35                  40                  45

Ala Thr Ile Ala Asp Gly Ser Ser Thr Asn Tyr Ala Asp Ser Val Lys
     50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Leu Gly Gln Val Ser Glu Tyr Asn Ser Ala Ser Tyr Glu Trp Thr
              100                 105                 110

Tyr Pro Tyr Trp Gly Gln Gly Thr Gln Val Thr Val Ser Ser
          115                 120                 125

<210> SEQ ID NO 12
<211> LENGTH: 9
<212> TYPE: PRT
<213> ORGANISM: Homo sapiens

<400> SEQUENCE: 12

Gly Thr Ile Phe Gln Val Gly Ser Met
1               5

<210> SEQ ID NO 13
<211> LENGTH: 14
<212> TYPE: PRT
<213> ORGANISM: Homo sapiens

<400> SEQUENCE: 13

Glu Phe Val Ala Thr Ile Ala Asp Gly Ser Ser Thr Asn Tyr
1               5                   10

<210> SEQ ID NO 14
<211> LENGTH: 20
<212> TYPE: PRT
<213> ORGANISM: Homo sapiens

<400> SEQUENCE: 14

Ala Ala Leu Gly Gln Val Ser Glu Tyr Asn Ser Ala Ser Tyr Glu Trp
1               5                   10                  15

Thr Tyr Pro Tyr
            20

<210> SEQ ID NO 15
<211> LENGTH: 118
<212> TYPE: PRT
<213> ORGANISM: Homo sapiens

<400> SEQUENCE: 15

Gln Val Gln Leu Gln Glu Ser Gly Gly Gly Leu Val Gln Ala Gly Gly
1               5                   10                  15

Ser Leu Arg Leu Ser Cys Ala Ala Ser Gly Asn Ile Phe Asn Glu Tyr
              20                  25                  30

Phe Met Gly Trp Tyr Arg Gln Ala Pro Gly Lys Glu Arg Glu Phe Val
              35                  40                  45

Ala Thr Ile Asp Gln Gly Ala Asn Thr Tyr Tyr Ala Asp Ser Val Lys
     50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95
```

-continued

```
Val Ile Gly Ser Asp Val Tyr Gly His Ala Tyr Trp Gly Gln Gly Thr
        100                 105                 110

Gln Val Thr Val Ser Ser
        115

<210> SEQ ID NO 16
<211> LENGTH: 9
<212> TYPE: PRT
<213> ORGANISM: Homo sapiens

<400> SEQUENCE: 16

Gly Asn Ile Phe Asn Glu Tyr Phe Met
1               5

<210> SEQ ID NO 17
<211> LENGTH: 14
<212> TYPE: PRT
<213> ORGANISM: Homo sapiens

<400> SEQUENCE: 17

Glu Phe Val Ala Thr Ile Asp Gln Gly Ala Asn Thr Tyr Tyr
1               5                   10

<210> SEQ ID NO 18
<211> LENGTH: 12
<212> TYPE: PRT
<213> ORGANISM: Homo sapiens

<400> SEQUENCE: 18

Ala Val Ile Gly Ser Asp Val Tyr Gly His Ala Tyr
1               5                   10

<210> SEQ ID NO 19
<211> LENGTH: 126
<212> TYPE: PRT
<213> ORGANISM: Homo sapiens

<400> SEQUENCE: 19

Gln Val Gln Leu Gln Glu Ser Gly Gly Gly Leu Val Gln Ala Gly Gly
1               5                   10                  15

Ser Leu Arg Leu Ser Cys Ala Ala Ser Gly Thr Ile Phe Gln Val Gly
            20                  25                  30

Ser Met Gly Trp Tyr Arg Gln Ala Pro Gly Lys Glu Arg Glu Phe Val
            35                  40                  45

Ala Thr Ile Ala Asp Gly Ser Ser Thr Asn Tyr Ala Asp Ser Val Lys
        50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Leu Gly Gln Val Ser Glu Tyr Asn Ser Ala Ser Tyr Glu Trp Thr
            100                 105                 110

Tyr Pro Tyr Trp Gly Gln Gly Thr Gln Val Thr Val Ser Ser
            115                 120                 125

<210> SEQ ID NO 20
<211> LENGTH: 9
<212> TYPE: PRT
<213> ORGANISM: Homo sapiens

<400> SEQUENCE: 20
```

```
Gly Thr Ile Phe Gln Val Gly Ser Met
1               5
```

```
<210> SEQ ID NO 21
<211> LENGTH: 14
<212> TYPE: PRT
<213> ORGANISM: Homo sapiens

<400> SEQUENCE: 21

Glu Phe Val Ala Thr Ile Ala Asp Gly Ser Ser Thr Asn Tyr
1               5                   10
```

```
<210> SEQ ID NO 22
<211> LENGTH: 20
<212> TYPE: PRT
<213> ORGANISM: Homo sapiens

<400> SEQUENCE: 22

Ala Ala Leu Gly Gln Val Ser Glu Tyr Asn Ser Ala Ser Tyr Glu Trp
1               5                   10                  15

Thr Tyr Pro Tyr
            20
```

```
<210> SEQ ID NO 23
<211> LENGTH: 122
<212> TYPE: PRT
<213> ORGANISM: Homo sapiens

<400> SEQUENCE: 23

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Phe Gly Ile Val
            20                  25                  30

Val Met Gly Trp Tyr Arg Gln Ala Pro Gly Lys Glu Arg Glu Phe Val
        35                  40                  45

Ala Ser Ile Asn Trp Gly Ala Asn Thr Tyr Tyr Ala Asp Ser Val Lys
        50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala His Trp His Tyr Asp Tyr Pro Tyr Asp Arg Asp Phe Leu Tyr Trp
                100                 105                 110

Gly Gln Gly Thr Gln Val Thr Val Ser Ser
            115                 120
```

```
<210> SEQ ID NO 24
<211> LENGTH: 9
<212> TYPE: PRT
<213> ORGANISM: Homo sapiens

<400> SEQUENCE: 24

Gly Ser Ile Phe Gly Ile Val Val Met
1               5
```

```
<210> SEQ ID NO 25
<211> LENGTH: 14
<212> TYPE: PRT
<213> ORGANISM: Homo sapiens

<400> SEQUENCE: 25
```

-continued

```
Glu Phe Val Ala Ser Ile Asn Trp Gly Ala Asn Thr Tyr Tyr
1               5                   10

<210> SEQ ID NO 26
<211> LENGTH: 16
<212> TYPE: PRT
<213> ORGANISM: Homo sapiens

<400> SEQUENCE: 26

Ala Ala His Trp His Tyr Asp Tyr Pro Tyr Asp Arg Asp Phe Leu Tyr
1               5                   10                  15

<210> SEQ ID NO 27
<211> LENGTH: 126
<212> TYPE: PRT
<213> ORGANISM: Homo sapiens

<400> SEQUENCE: 27

Gln Val Gln Leu Gln Glu Ser Gly Gly Gly Leu Val Gln Ala Gly Gly
1               5                   10                  15

Ser Leu Arg Leu Ser Cys Ala Ala Ser Gly Thr Ile Phe Tyr Thr Arg
            20                  25                  30

Asp Met Gly Trp Tyr Arg Gln Ala Pro Gly Lys Glu Arg Glu Leu Val
        35                  40                  45

Ala Ala Ile Thr Ala Gly Ala Asn Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Tyr Pro Asn Ala Pro Asp Ile Ser Asp Glu Asp Tyr Asn Glu Gly
            100                 105                 110

Tyr Leu Tyr Trp Gly Gln Gly Thr Gln Val Thr Val Ser Ser
        115                 120                 125

<210> SEQ ID NO 28
<211> LENGTH: 9
<212> TYPE: PRT
<213> ORGANISM: Homo sapiens

<400> SEQUENCE: 28

Gly Thr Ile Phe Tyr Thr Arg Asp Met
1               5

<210> SEQ ID NO 29
<211> LENGTH: 14
<212> TYPE: PRT
<213> ORGANISM: Homo sapiens

<400> SEQUENCE: 29

Glu Leu Val Ala Ala Ile Thr Ala Gly Ala Asn Thr Tyr Tyr
1               5                   10

<210> SEQ ID NO 30
<211> LENGTH: 20
<212> TYPE: PRT
<213> ORGANISM: Homo sapiens

<400> SEQUENCE: 30

Ala Ala Tyr Pro Asn Ala Pro Asp Ile Ser Asp Glu Asp Tyr Asn Glu
1               5                   10                  15
```

-continued

```
Gly Tyr Leu Tyr
        20

<210> SEQ ID NO 31
<211> LENGTH: 126
<212> TYPE: PRT
<213> ORGANISM: Homo sapiens

<400> SEQUENCE: 31

Gln Val Gln Leu Gln Glu Ser Gly Gly Gly Leu Val Gln Ala Gly Gly
1               5                   10                  15

Ser Leu Arg Leu Ser Cys Ala Ala Ser Gly Thr Ile Phe Ser Trp Lys
            20                  25                  30

Thr Met Gly Trp Tyr Arg Gln Ala Pro Gly Lys Glu Arg Glu Phe Val
        35                  40                  45

Ala Ser Ile Asn Gly Gly Thr Asn Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
            85                  90                  95

Ala Ser Arg Pro Asn Ile Pro Phe Arg Ala Asp Tyr Tyr Asp Gln Arg
            100                 105                 110

His Thr Tyr Trp Gly Gln Gly Thr Gln Val Thr Val Ser Ser
        115                 120                 125

<210> SEQ ID NO 32
<211> LENGTH: 9
<212> TYPE: PRT
<213> ORGANISM: Homo sapiens

<400> SEQUENCE: 32

Gly Thr Ile Phe Ser Trp Lys Thr Met
1               5

<210> SEQ ID NO 33
<211> LENGTH: 14
<212> TYPE: PRT
<213> ORGANISM: Homo sapiens

<400> SEQUENCE: 33

Glu Phe Val Ala Ser Ile Asn Gly Gly Thr Asn Thr Asn Tyr
1               5                   10

<210> SEQ ID NO 34
<211> LENGTH: 20
<212> TYPE: PRT
<213> ORGANISM: Homo sapiens

<400> SEQUENCE: 34

Ala Ala Ser Arg Pro Asn Ile Pro Phe Arg Ala Asp Tyr Tyr Asp Gln
1               5                   10                  15

Arg His Thr Tyr
        20

<210> SEQ ID NO 35
<211> LENGTH: 126
<212> TYPE: PRT
<213> ORGANISM: Homo sapiens

<400> SEQUENCE: 35
```

-continued

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Ser Arg Asp Tyr
            20                  25                  30

Asp Met Gly Trp Tyr Arg Gln Ala Pro Gly Lys Glu Arg Glu Phe Val
            35                  40                  45

Ala Gly Ile Asn Val Gly Gly Thr Thr Asn Tyr Ala Asp Ser Val Lys
        50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Val His Ala Val Tyr Thr Asp Gly Trp Glu Asp Gly Tyr Leu Tyr Pro
                100                 105                 110

Leu Pro Tyr Trp Gly Gln Gly Thr Gln Val Thr Val Ser Ser
                115                 120                 125
```

<210> SEQ ID NO 36
<211> LENGTH: 9
<212> TYPE: PRT
<213> ORGANISM: Homo sapiens

<400> SEQUENCE: 36

```
Gly Ser Ile Ser Arg Asp Tyr Asp Met
1               5
```

<210> SEQ ID NO 37
<211> LENGTH: 14
<212> TYPE: PRT
<213> ORGANISM: Homo sapiens

<400> SEQUENCE: 37

```
Glu Phe Val Ala Gly Ile Asn Val Gly Gly Thr Thr Asn Tyr
1               5                   10
```

<210> SEQ ID NO 38
<211> LENGTH: 20
<212> TYPE: PRT
<213> ORGANISM: Homo sapiens

<400> SEQUENCE: 38

```
Ala Val His Ala Val Tyr Thr Asp Gly Trp Glu Asp Gly Tyr Leu Tyr
1               5                   10                  15

Pro Leu Pro Tyr
            20
```

<210> SEQ ID NO 39
<211> LENGTH: 126
<212> TYPE: PRT
<213> ORGANISM: Homo sapiens

<400> SEQUENCE: 39

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Thr Ile Ser Tyr Thr Pro
            20                  25                  30

Ile Met Gly Trp Tyr Arg Gln Ala Pro Gly Lys Glu Arg Glu Phe Val
            35                  40                  45

Ala Thr Ile Ala Leu Gly Thr Thr Thr Asn Tyr Ala Asp Ser Val Lys
        50                  55                  60
```

-continued

```
Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Val Val Ser Phe Ala Thr Thr Arg Tyr Asp Pro Val Phe Thr Asp Thr
                100                 105                 110

Leu Pro Tyr Trp Gly Gln Gly Thr Gln Val Thr Val Ser Ser
        115                 120                 125

<210> SEQ ID NO 40
<211> LENGTH: 9
<212> TYPE: PRT
<213> ORGANISM: Homo sapiens

<400> SEQUENCE: 40

Gly Thr Ile Ser Tyr Thr Pro Ile Met
1               5

<210> SEQ ID NO 41
<211> LENGTH: 14
<212> TYPE: PRT
<213> ORGANISM: Homo sapiens

<400> SEQUENCE: 41

Glu Phe Val Ala Thr Ile Ala Leu Gly Thr Thr Thr Asn Tyr
1               5                   10

<210> SEQ ID NO 42
<211> LENGTH: 20
<212> TYPE: PRT
<213> ORGANISM: Homo sapiens

<400> SEQUENCE: 42

Ala Val Val Ser Phe Ala Thr Thr Arg Tyr Asp Pro Val Phe Thr Asp
1               5                   10                  15

Thr Leu Pro Tyr
            20

<210> SEQ ID NO 43
<211> LENGTH: 126
<212> TYPE: PRT
<213> ORGANISM: Homo sapiens

<400> SEQUENCE: 43

Gln Val Gln Leu Gln Glu Ser Gly Gly Gly Leu Val Gln Ala Gly Gly
1               5                   10                  15

Ser Leu Arg Leu Ser Cys Ala Ala Ser Gly Thr Ile Phe Gln Val Ser
                20                  25                  30

Ser Met Gly Trp Tyr Arg Gln Ala Pro Gly Lys Glu Arg Lys Phe Val
        35                  40                  45

Ala Thr Ile Ala Asp Gly Ser Ser Thr Asn Tyr Ala Gly Ser Val Lys
        50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Leu Gly Gln Val Ser Glu Tyr Asn Ser Ala Ser Tyr Glu Trp Thr
                100                 105                 110

Tyr Pro Tyr Trp Gly Gln Gly Thr Gln Val Thr Val Ser Ser
```

-continued

```
              115                 120                 125

<210> SEQ ID NO 44
<211> LENGTH: 9
<212> TYPE: PRT
<213> ORGANISM: Homo sapiens

<400> SEQUENCE: 44

Gly Thr Ile Phe Gln Val Ser Ser Met
1               5

<210> SEQ ID NO 45
<211> LENGTH: 14
<212> TYPE: PRT
<213> ORGANISM: Homo sapiens

<400> SEQUENCE: 45

Lys Phe Val Ala Thr Ile Ala Asp Gly Ser Ser Thr Asn Tyr
1               5                   10

<210> SEQ ID NO 46
<211> LENGTH: 20
<212> TYPE: PRT
<213> ORGANISM: Homo sapiens

<400> SEQUENCE: 46

Ala Ala Leu Gly Gln Val Ser Glu Tyr Asn Ser Ala Ser Tyr Glu Trp
1               5                   10                  15

Thr Tyr Pro Tyr
            20

<210> SEQ ID NO 47
<211> LENGTH: 126
<212> TYPE: PRT
<213> ORGANISM: Homo sapiens

<400> SEQUENCE: 47

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Ser Arg Asp Tyr
            20                  25                  30

Asp Met Gly Trp Tyr Arg Gln Ala Pro Gly Lys Glu Arg Lys Phe Val
            35                  40                  45

Ala Gly Ile Asn Val Gly Gly Thr Thr Asn Tyr Ala Gly Ser Val Lys
        50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Val His Ala Val Tyr Thr Asp Gly Trp Glu Asp Gly Tyr Leu Tyr Pro
                100                 105                 110

Leu Pro Tyr Trp Gly Gln Gly Thr Gln Val Thr Val Ser Ser
            115                 120                 125

<210> SEQ ID NO 48
<211> LENGTH: 9
<212> TYPE: PRT
<213> ORGANISM: Homo sapiens

<400> SEQUENCE: 48

Gly Ser Ile Ser Arg Asp Tyr Asp Met
```

-continued

```
1                5

<210> SEQ ID NO 49
<211> LENGTH: 14
<212> TYPE: PRT
<213> ORGANISM: Homo sapiens

<400> SEQUENCE: 49

Lys Phe Val Ala Gly Ile Asn Val Gly Gly Thr Thr Asn Tyr
1                5                   10

<210> SEQ ID NO 50
<211> LENGTH: 20
<212> TYPE: PRT
<213> ORGANISM: Homo sapiens

<400> SEQUENCE: 50

Ala Val His Ala Val Tyr Thr Asp Gly Trp Glu Asp Gly Tyr Leu Tyr
1                5                   10                  15

Pro Leu Pro Tyr
            20

<210> SEQ ID NO 51
<211> LENGTH: 126
<212> TYPE: PRT
<213> ORGANISM: Homo sapiens

<400> SEQUENCE: 51

Gln Val Gln Leu Gln Glu Ser Gly Gly Gly Leu Val Gln Ala Gly Gly
1                5                   10                  15

Ser Leu Arg Leu Ser Cys Ala Ala Ser Gly Thr Ile Ser Tyr Thr Pro
            20                  25                  30

Ile Met Gly Trp Tyr Arg Gln Ala Pro Gly Lys Glu Arg Lys Phe Val
            35                  40                  45

Ala Thr Ile Ala Leu Gly Thr Thr Thr Asn Tyr Ala Gly Ser Val Lys
            50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
            85                  90                  95

Val Val Ser Phe Ala Thr Thr Arg Tyr Asp Pro Val Phe Thr Asp Thr
            100                 105                 110

Leu Pro Tyr Trp Gly Gln Gly Thr Gln Val Thr Val Ser Ser
            115                 120                 125

<210> SEQ ID NO 52
<211> LENGTH: 9
<212> TYPE: PRT
<213> ORGANISM: Homo sapiens

<400> SEQUENCE: 52

Gly Thr Ile Ser Tyr Thr Pro Ile Met
1                5

<210> SEQ ID NO 53
<211> LENGTH: 14
<212> TYPE: PRT
<213> ORGANISM: Homo sapiens

<400> SEQUENCE: 53

Lys Phe Val Ala Thr Ile Ala Leu Gly Thr Thr Thr Asn Tyr
```

```
1               5                    10
```

<210> SEQ ID NO 54
<211> LENGTH: 20
<212> TYPE: PRT
<213> ORGANISM: Homo sapiens

<400> SEQUENCE: 54

```
Ala Val Val Ser Phe Ala Thr Thr Arg Tyr Asp Pro Val Phe Thr Asp
1               5                    10                   15

Thr Leu Pro Tyr
            20
```

<210> SEQ ID NO 55
<211> LENGTH: 127
<212> TYPE: PRT
<213> ORGANISM: Homo sapiens

<400> SEQUENCE: 55

```
Gln Val Gln Leu Gln Glu Ser Gly Gly Gly Leu Val Gln Ala Gly Gly
1               5                    10                   15

Ser Leu Arg Leu Ser Cys Ala Ala Ser Gly Asn Ile Ser Tyr Tyr Arg
            20                   25                   30

His Met Gly Trp Tyr Arg Gln Ala Pro Gly Lys Glu Arg Glu Leu Val
        35                   40                   45

Ala Ser Ile Gly Asp Gly Gly Asn Thr Asn Tyr Ala Asp Ser Val Lys
    50                   55                   60

Gly Arg Phe Thr Ile Ser Arg Asp Asn Ala Lys Asn Thr Val Tyr Leu
65                   70                   75                   80

Gln Met Asn Ser Leu Lys Pro Glu Asp Thr Ala Val Tyr Tyr Cys Ala
                85                   90                   95

Val Val His Asn Thr Tyr Leu Leu Tyr Asp Pro Tyr Val Trp Asp Tyr
            100                  105                  110

Leu Leu Leu Tyr Trp Gly Gln Gly Thr Gln Val Thr Val Ser Ser
        115                  120                  125
```

<210> SEQ ID NO 56
<211> LENGTH: 9
<212> TYPE: PRT
<213> ORGANISM: Homo sapiens

<400> SEQUENCE: 56

```
Gly Asn Ile Ser Tyr Tyr Arg His Met
1               5
```

<210> SEQ ID NO 57
<211> LENGTH: 14
<212> TYPE: PRT
<213> ORGANISM: Homo sapiens

<400> SEQUENCE: 57

```
Glu Leu Val Ala Ser Ile Gly Asp Gly Gly Asn Thr Asn Tyr
1               5                    10
```

<210> SEQ ID NO 58
<211> LENGTH: 21
<212> TYPE: PRT
<213> ORGANISM: Homo sapiens

<400> SEQUENCE: 58

```
Ala Val Val His Asn Thr Tyr Leu Leu Tyr Asp Pro Tyr Val Trp Asp
```

```
1               5               10              15

Tyr Leu Leu Leu Tyr
            20

<210> SEQ ID NO 59
<211> LENGTH: 118
<212> TYPE: PRT
<213> ORGANISM: Homo sapiens

<400> SEQUENCE: 59

Gln Val Gln Leu Gln Glu Ser Gly Gly Gly Leu Val Gln Ala Gly Gly
1               5               10              15

Ser Leu Arg Leu Ser Cys Ala Ala Ser Gly Asn Ile Ser Tyr Asp Trp
            20              25              30

Tyr Met Gly Trp Tyr Arg Gln Ala Pro Gly Lys Glu Arg Glu Phe Val
        35              40              45

Ala Ser Ile Asn Arg Gly Ala Thr Thr Asn Tyr Ala Asp Ser Val Lys
    50              55              60

Gly Arg Phe Thr Ile Ser Arg Asp Asn Ala Lys Asn Thr Val Tyr Leu
65              70              75              80

Gln Met Asn Ser Leu Lys Pro Glu Asp Thr Ala Val Tyr Tyr Cys Ala
            85              90              95

Val Asp Asp Tyr Ser Asp Asp Trp Tyr Gly Tyr Trp Gly Gln Gly Thr
            100             105             110

Gln Val Thr Val Ser Ser
        115

<210> SEQ ID NO 60
<211> LENGTH: 9
<212> TYPE: PRT
<213> ORGANISM: Homo sapiens

<400> SEQUENCE: 60

Gly Asn Ile Ser Tyr Asp Trp Tyr Met
1               5

<210> SEQ ID NO 61
<211> LENGTH: 14
<212> TYPE: PRT
<213> ORGANISM: Homo sapiens

<400> SEQUENCE: 61

Glu Phe Val Ala Ser Ile Asn Arg Gly Ala Thr Thr Asn Tyr
1               5               10

<210> SEQ ID NO 62
<211> LENGTH: 12
<212> TYPE: PRT
<213> ORGANISM: Homo sapiens

<400> SEQUENCE: 62

Ala Val Asp Asp Tyr Ser Asp Asp Trp Tyr Gly Tyr
1               5               10

<210> SEQ ID NO 63
<211> LENGTH: 127
<212> TYPE: PRT
<213> ORGANISM: Homo sapiens

<400> SEQUENCE: 63

Gln Val Gln Leu Gln Glu Ser Gly Gly Gly Leu Val Gln Ala Gly Gly
```

-continued

```
1               5                   10                  15

Ser Leu Arg Leu Ser Cys Ala Ala Ser Gly Asn Ile Ser Tyr Tyr Arg
            20                  25                  30

Arg Met Gly Trp Tyr Arg Gln Ala Pro Gly Lys Glu Arg Glu Leu Val
            35                  40                  45

Ala Ser Ile Gly Asp Gly Gly Asn Thr Asn Tyr Ala Asp Ser Val Lys
            50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Val Val Arg Lys Thr Tyr Leu Leu Tyr Asp Pro Tyr Val Trp Tyr Tyr
                100                 105                 110

Val Leu Leu Tyr Trp Gly Gln Gly Thr Gln Val Thr Val Ser Ser
                115                 120                 125
```

```
<210> SEQ ID NO 64
<211> LENGTH: 9
<212> TYPE: PRT
<213> ORGANISM: Homo sapiens

<400> SEQUENCE: 64

Gly Asn Ile Ser Tyr Tyr Arg Arg Met
1               5
```

```
<210> SEQ ID NO 65
<211> LENGTH: 14
<212> TYPE: PRT
<213> ORGANISM: Homo sapiens

<400> SEQUENCE: 65

Glu Leu Val Ala Ser Ile Gly Asp Gly Gly Asn Thr Asn Tyr
1               5                   10
```

```
<210> SEQ ID NO 66
<211> LENGTH: 21
<212> TYPE: PRT
<213> ORGANISM: Homo sapiens

<400> SEQUENCE: 66

Ala Val Val Arg Lys Thr Tyr Leu Leu Tyr Asp Pro Tyr Val Trp Tyr
1               5                   10                  15

Tyr Val Leu Leu Tyr
            20
```

```
<210> SEQ ID NO 67
<211> LENGTH: 118
<212> TYPE: PRT
<213> ORGANISM: Homo sapiens

<400> SEQUENCE: 67

Gln Val Gln Leu Gln Glu Ser Gly Gly Gly Leu Val Gln Ala Gly Gly
1               5                   10                  15

Ser Leu Arg Leu Ser Cys Ala Ala Ser Gly Asn Ile Ser Pro Thr Tyr
            20                  25                  30

Leu Met Gly Trp Tyr Arg Gln Ala Pro Gly Lys Glu Arg Glu Phe Val
            35                  40                  45

Ala Gly Ile Ala His Gly Ala Ser Thr Asn Tyr Ala Asp Ser Val Lys
            50                  55                  60
```

```
Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Val Asn Pro Tyr Ala Leu Asp Val Leu Val Tyr Trp Gly Gln Gly Thr
            100                 105                 110

Gln Val Thr Val Ser Ser
        115

<210> SEQ ID NO 68
<211> LENGTH: 9
<212> TYPE: PRT
<213> ORGANISM: Homo sapiens

<400> SEQUENCE: 68

Gly Asn Ile Ser Pro Thr Tyr Leu Met
1               5

<210> SEQ ID NO 69
<211> LENGTH: 14
<212> TYPE: PRT
<213> ORGANISM: Homo sapiens

<400> SEQUENCE: 69

Glu Phe Val Ala Gly Ile Ala His Gly Ala Ser Thr Asn Tyr
1               5                   10

<210> SEQ ID NO 70
<211> LENGTH: 12
<212> TYPE: PRT
<213> ORGANISM: Homo sapiens

<400> SEQUENCE: 70

Ala Val Asn Pro Tyr Ala Leu Asp Val Leu Val Tyr
1               5                   10

<210> SEQ ID NO 71
<211> LENGTH: 122
<212> TYPE: PRT
<213> ORGANISM: Homo sapiens

<400> SEQUENCE: 71

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Phe Leu Pro Pro
                20                  25                  30

Tyr Met Gly Trp Tyr Arg Gln Ala Pro Gly Lys Glu Arg Glu Phe Val
                35                  40                  45

Ala Gly Ile Gly Gly Gly Ser Ser Thr Tyr Tyr Ala Asp Ser Val Lys
            50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Val Val Tyr Tyr Thr Asp Pro Ser Asp Glu Phe Ala His Tyr Tyr Trp
            100                 105                 110

Gly Gln Gly Thr Gln Val Thr Val Ser Ser
        115                 120

<210> SEQ ID NO 72
```

```
<211> LENGTH: 9
<212> TYPE: PRT
<213> ORGANISM: Homo sapiens

<400> SEQUENCE: 72

Gly Ser Ile Phe Leu Pro Pro Tyr Met
1               5

<210> SEQ ID NO 73
<211> LENGTH: 14
<212> TYPE: PRT
<213> ORGANISM: Homo sapiens

<400> SEQUENCE: 73

Glu Phe Val Ala Gly Ile Gly Gly Gly Ser Ser Thr Tyr Tyr
1               5                   10

<210> SEQ ID NO 74
<211> LENGTH: 16
<212> TYPE: PRT
<213> ORGANISM: Homo sapiens

<400> SEQUENCE: 74

Ala Val Val Tyr Tyr Thr Asp Pro Ser Asp Glu Phe Ala His Tyr Tyr
1               5                   10                  15

<210> SEQ ID NO 75
<211> LENGTH: 119
<212> TYPE: PRT
<213> ORGANISM: Homo sapiens

<400> SEQUENCE: 75

Gln Val Gln Leu Gln Glu Ser Gly Gly Gly Leu Val Gln Ala Gly Gly
1               5                   10                  15

Ser Leu Arg Leu Ser Cys Ala Ala Ser Gly Thr Ile Ser Arg Tyr Ile
            20                  25                  30

Tyr Met Gly Trp Tyr Arg Gln Ala Pro Gly Lys Glu Arg Glu Phe Val
            35                  40                  45

Ala Ser Ile Ala Arg Gly Thr Ile Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Asp Asn Lys Tyr Glu Asp Ala Tyr Tyr Gly Tyr Trp Gly Gln Gly
                100                 105                 110

Thr Gln Val Thr Val Ser Ser
        115

<210> SEQ ID NO 76
<211> LENGTH: 9
<212> TYPE: PRT
<213> ORGANISM: Homo sapiens

<400> SEQUENCE: 76

Gly Thr Ile Ser Arg Tyr Ile Tyr Met
1               5

<210> SEQ ID NO 77
<211> LENGTH: 14
<212> TYPE: PRT
<213> ORGANISM: Homo sapiens
```

<400> SEQUENCE: 77

Glu Phe Val Ala Ser Ile Ala Arg Gly Thr Ile Thr Tyr Tyr
1               5                   10

<210> SEQ ID NO 78
<211> LENGTH: 13
<212> TYPE: PRT
<213> ORGANISM: Homo sapiens

<400> SEQUENCE: 78

Ala Ala Asp Asn Lys Tyr Glu Asp Ala Tyr Tyr Gly Tyr
1               5                   10

<210> SEQ ID NO 79
<211> LENGTH: 118
<212> TYPE: PRT
<213> ORGANISM: Homo sapiens

<400> SEQUENCE: 79

Gln Val Gln Leu Gln Glu Ser Gly Gly Gly Leu Val Gln Ala Gly Gly
1               5                   10                  15

Ser Leu Arg Leu Ser Cys Ala Ala Ser Gly Asn Ile Ser Pro Thr Asn
            20                  25                  30

Leu Met Gly Trp Tyr Arg Gln Ala Pro Gly Lys Glu Arg Glu Phe Val
            35                  40                  45

Ala Ala Ile Ala His Gly Ala Ser Thr Asn Tyr Ala Asp Ser Val Lys
        50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Val
                85                  90                  95

Val Asn Pro Tyr Ala Leu Asp Val Leu Val Tyr Trp Gly Gln Gly Thr
                100                 105                 110

Gln Val Thr Val Ser Ser
        115

<210> SEQ ID NO 80
<211> LENGTH: 9
<212> TYPE: PRT
<213> ORGANISM: Homo sapiens

<400> SEQUENCE: 80

Gly Asn Ile Ser Pro Thr Asn Leu Met
1               5

<210> SEQ ID NO 81
<211> LENGTH: 14
<212> TYPE: PRT
<213> ORGANISM: Homo sapiens

<400> SEQUENCE: 81

Glu Phe Val Ala Ala Ile Ala His Gly Ala Ser Thr Asn Tyr
1               5                   10

<210> SEQ ID NO 82
<211> LENGTH: 12
<212> TYPE: PRT
<213> ORGANISM: Homo sapiens

<400> SEQUENCE: 82

```
Val Val Asn Pro Tyr Ala Leu Asp Val Leu Val Tyr
1               5                   10

<210> SEQ ID NO 83
<211> LENGTH: 118
<212> TYPE: PRT
<213> ORGANISM: Homo sapiens

<400> SEQUENCE: 83

Gln Val Gln Leu Gln Glu Ser Gly Gly Gly Leu Val Gln Ala Gly Gly
1               5                   10                  15

Ser Leu Arg Leu Ser Cys Ala Ala Ser Gly Thr Ile Ser Tyr Thr Pro
            20                  25                  30

Ile Met Gly Trp Tyr Arg Gln Ala Pro Gly Lys Glu Arg Glu Phe Val
        35                  40                  45

Ala Ala Ile Ala His Gly Ala Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Val Asn Pro Tyr Ala Leu Asp Val Leu Val Tyr Trp Gly Gln Gly Thr
            100                 105                 110

Gln Val Thr Val Ser Ser
        115

<210> SEQ ID NO 84
<211> LENGTH: 9
<212> TYPE: PRT
<213> ORGANISM: Homo sapiens

<400> SEQUENCE: 84

Gly Thr Ile Ser Tyr Thr Pro Ile Met
1               5

<210> SEQ ID NO 85
<211> LENGTH: 14
<212> TYPE: PRT
<213> ORGANISM: Homo sapiens

<400> SEQUENCE: 85

Glu Phe Val Ala Ala Ile Ala His Gly Ala Ser Thr Asn Tyr
1               5                   10

<210> SEQ ID NO 86
<211> LENGTH: 12
<212> TYPE: PRT
<213> ORGANISM: Homo sapiens

<400> SEQUENCE: 86

Ala Val Asn Pro Tyr Ala Leu Asp Val Leu Val Tyr
1               5                   10

<210> SEQ ID NO 87
<211> LENGTH: 118
<212> TYPE: PRT
<213> ORGANISM: Mesocricetus auratus

<400> SEQUENCE: 87

Gln Val Gln Leu Gln Glu Ser Gly Gly Gly Leu Val Gln Ala Gly Gly
1               5                   10                  15
```

-continued

```
Ser Leu Arg Leu Ser Cys Ala Ala Ser Gly Asn Ile Ser Pro Glu Tyr
        20                  25                  30

Arg Met Gly Trp Tyr Arg Gln Ala Pro Gly Lys Glu Arg Glu Phe Val
        35                  40                  45

Ala Gly Ile Asp Tyr Gly Gly Asn Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Val Arg Thr Tyr Asp Gly Gly Thr His Thr Tyr Trp Gly Gln Gly Thr
            100                 105                 110

Gln Val Thr Val Ser Ser
        115
```

```
<210> SEQ ID NO 88
<211> LENGTH: 9
<212> TYPE: PRT
<213> ORGANISM: Mesocricetus auratus

<400> SEQUENCE: 88

Gly Asn Ile Ser Pro Glu Tyr Arg Met
1               5
```

```
<210> SEQ ID NO 89
<211> LENGTH: 14
<212> TYPE: PRT
<213> ORGANISM: Mesocricetus auratus

<400> SEQUENCE: 89

Glu Phe Val Ala Gly Ile Asp Tyr Gly Gly Asn Thr Tyr Tyr
1               5                   10
```

```
<210> SEQ ID NO 90
<211> LENGTH: 12
<212> TYPE: PRT
<213> ORGANISM: Mesocricetus auratus

<400> SEQUENCE: 90

Ala Val Arg Thr Tyr Asp Gly Gly Thr His Thr Tyr
1               5                   10
```

```
<210> SEQ ID NO 91
<211> LENGTH: 118
<212> TYPE: PRT
<213> ORGANISM: Mesocricetus auratus

<400> SEQUENCE: 91

Gln Val Gln Leu Gln Glu Ser Gly Gly Gly Leu Val Gln Ala Gly Gly
1               5                   10                  15

Ser Leu Arg Leu Ser Cys Ala Ala Ser Gly Asn Ile Ser Pro Thr Tyr
        20                  25                  30

Leu Met Gly Trp Tyr Arg Gln Ala Pro Gly Lys Glu Arg Glu Phe Val
        35                  40                  45

Ala Gly Ile Ala His Gly Ala Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95
```

-continued

Val Asn Pro Tyr Ala Leu Asp Val Leu Val Tyr Trp Gly Gln Gly Thr
                100                 105                 110

Gln Val Thr Val Ser Ser
        115

<210> SEQ ID NO 92
<211> LENGTH: 9
<212> TYPE: PRT
<213> ORGANISM: Mesocricetus auratus

<400> SEQUENCE: 92

Gly Asn Ile Ser Pro Thr Tyr Leu Met
1               5

<210> SEQ ID NO 93
<211> LENGTH: 14
<212> TYPE: PRT
<213> ORGANISM: Mesocricetus auratus

<400> SEQUENCE: 93

Glu Phe Val Ala Gly Ile Ala His Gly Ala Ser Thr Asn Tyr
1               5                   10

<210> SEQ ID NO 94
<211> LENGTH: 12
<212> TYPE: PRT
<213> ORGANISM: Mesocricetus auratus

<400> SEQUENCE: 94

Ala Val Asn Pro Tyr Ala Leu Asp Val Leu Val Tyr
1               5                   10

<210> SEQ ID NO 95
<211> LENGTH: 113
<212> TYPE: PRT
<213> ORGANISM: Mus musculus

<400> SEQUENCE: 95

Gln Val Gln Leu Gln Glu Ser Gly Gly Gly Leu Val Gln Ala Gly Gly
1               5                   10                  15

Ser Leu Arg Leu Ser Cys Ala Ala Ser Gly Asn Ile Phe Tyr Ile Pro
            20                  25                  30

Val Met Gly Trp Tyr Arg Gln Ala Pro Gly Lys Glu Arg Glu Phe Val
            35                  40                  45

Ala Ala Ile Ala Tyr Gly Thr Thr Thr Asn Tyr Ala Asp Ser Val Lys
        50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Val Ala Tyr Tyr Thr Tyr Trp Gly Gln Gly Thr Gln Val Thr Val Ser
            100                 105                 110

Ser

<210> SEQ ID NO 96
<211> LENGTH: 9
<212> TYPE: PRT
<213> ORGANISM: Mus musculus

<400> SEQUENCE: 96

-continued

```
Gly Asn Ile Phe Tyr Ile Pro Val Met
1               5

<210> SEQ ID NO 97
<211> LENGTH: 14
<212> TYPE: PRT
<213> ORGANISM: Mus musculus

<400> SEQUENCE: 97

Glu Phe Val Ala Ala Ile Ala Tyr Gly Thr Thr Thr Asn Tyr
1               5                   10

<210> SEQ ID NO 98
<211> LENGTH: 7
<212> TYPE: PRT
<213> ORGANISM: Mus musculus

<400> SEQUENCE: 98

Ala Val Ala Tyr Tyr Thr Tyr
1               5

<210> SEQ ID NO 99
<211> LENGTH: 113
<212> TYPE: PRT
<213> ORGANISM: Mus musculus

<400> SEQUENCE: 99

Gln Val Gln Leu Gln Glu Ser Gly Gly Gly Leu Val Gln Ala Gly Gly
1               5                   10                  15

Ser Leu Arg Leu Ser Cys Ala Ala Ser Gly Thr Ile Ser Pro Ala Pro
            20                  25                  30

Ile Met Gly Trp Tyr Arg Gln Ala Pro Gly Lys Glu Arg Glu Phe Val
            35                  40                  45

Ala Ala Ile Asn His Gly Ala Ile Thr Tyr Tyr Ala Asp Ser Val Lys
        50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Val Tyr Pro His Ser Tyr Trp Gly Gln Gly Thr Gln Val Thr Val Ser
                100                 105                 110

Ser

<210> SEQ ID NO 100
<211> LENGTH: 9
<212> TYPE: PRT
<213> ORGANISM: Mus musculus

<400> SEQUENCE: 100

Gly Thr Ile Ser Pro Ala Pro Ile Met
1               5

<210> SEQ ID NO 101
<211> LENGTH: 14
<212> TYPE: PRT
<213> ORGANISM: Mus musculus

<400> SEQUENCE: 101

Glu Phe Val Ala Ala Ile Asn His Gly Ala Ile Thr Tyr Tyr
1               5                   10
```

-continued

```
<210> SEQ ID NO 102
<211> LENGTH: 7
<212> TYPE: PRT
<213> ORGANISM: Mus musculus

<400> SEQUENCE: 102

Ala Val Tyr Pro His Ser Tyr
1               5
```

AEROSOLIZED MUCUS-TETHERING NANOBODIES TO PROTECT AGAINST VIRAL AND MICROBIAL CONTAMINATION IN CLOSED AND SEMI-ENCLOSED SPACES

CROSS-REFERENCE TO RELATED APPLICATIONS

The present application claims the benefit of and priority to U.S. Provisional Patent Application No. 63/031,443 filed May 28, 2020, the entire disclosure of which is hereby incorporated by reference herein in its entireties for all purposes.

BACKGROUND

The recent emergence of the SARS-coronavirus 2 (SARS-CoV2) in Wuhan, China in December 2019, and its rapid international spread poses a major global crisis with more than 5.1 million cases and 335,000 deaths to date. COVID-19 presents with a spectrum of clinical phenotypes, with most patients exhibiting mild-to-moderate symptoms, and 15% progressing typically in a week to severe or critical disease that needs hospitalization, and a minority of those progressing to develop acute respiratory disease syndrome (ARDS) requiring mechanical ventilation. Epidemiological data so far suggest that COVID-19 has case fatality rate of about 2.3%, several times greater than that of seasonal influenza. The elderly and individuals with underlying medical comorbidities such as cardiovascular disease, diabetes mellitus, chronic lung disease, chronic kidney disease, obesity, hypertension or cancer have a much higher mortality rate than healthy young adults.

There is a critical need for new methods to minimize community spread of COVID19. The COVID19 coronavirus is highly contagious, and aerosolized viral particles released by infected cells of the respiratory pathways have been shown to readily contaminate exposed surfaces on objects or skin; and mucous membranes in the eyes, nose, and oral surfaces of individuals within close proximity of an infected person. COVID19 viral particles have been shown to retain their infectivity on surfaces for as long as 2 weeks and up to 48 hours suspended in air as aerosolized particles.

Personal protective equipment (PPE) and social distancing can help limit spread and exposure. However, many situations in normal life, including dining, restroom use, airline travel and most social interactions are disrupted or even prevented by these precautions. Efficacious treatments for infected individuals, and vaccines have yet to be developed. Alarmingly, some new research suggests that recovered or asymptomatic individuals could still be infectious thus increasing prospects of recurrences in the pandemic. While disinfectants are effective for decontaminating the skin or contact surfaces, no effective method exists for prophylaxis on mucous membranes where the virus infection starts.

SARS-CoV2 is known to gain entry into epithelial cells through the association of its viral spike protein with the ACE2 receptor, which is widely expressed on epithelial cell types. Targeting the interaction between spike protein and ACE2 by intravenous delivery of antibodies, or engineered such as decoy proteins such as soluble ACE2 receptor are promising approaches towards therapies, particularly in view of early indications that convalescent plasma is also effective. However it is unlikely that many of these therapies will become available in the near-term given the lengthy periods required for clinical testing.

Compositions and methods for reducing infection by SARS-CoV2 are of great interest. The present disclosure addresses this need.

SUMMARY

Compositions and methods are provided that relate to engineered nanobody-based platform for aerosolized dispersal of bispecific proteins that tether viral particles in the mucosal layer of exposed surfaces for inactivation, e.g. the eye, nose, throat, mouth, etc. The bispecific proteins may also be applied to inanimate surfaces, e.g. seats, telephones, countertops, knobs, etc., to reduce penetration and infection by airborne infectious virus. Airborne infectious viruses can, for example, for an infectious bioaerosol, and cause respiratory infections. Examples of airborne infectious virus include, without limitation, coronavirus, e.g. SARS-CoV; SARS-CoV2, MERS-CoV; measles morbillivirus (MeV); influenza virus, etc.

The bispecific proteins of the present disclosure comprise two different antigen binding regions (ABR), which are typically configured as immunoglobulin "single variable domains" (ISV). As used herein, ISV is used as a general term to include but not be limited to antigen-binding domains or fragments such as $V_{HH}$ domains or $V_H$ or $V_L$ domains, respectively. A first ISV of the bispecific protein specifically binds to a surface protein found on an airborne infectious virus. Target surface proteins on airborne viruses that find use in the present disclosure, include without limitation, a SARS-CoV spike protein, a SARS-CoV2 spike protein, a MERS-CoV spike protein, Influenza A virus hemagglutinin, etc. In an embodiment, a first ISV of the bispecific protein specifically binds to a conserved domain in the spike envelope protein encoded by SARS-CoV2, exemplified by the sequence at residues 387-516 of the spike protein, and as shown in FIG. 2. In some embodiments the ISV cross-reacts with additional coronavirus spike proteins, including SARS-CoV and MERS-CoV spike proteins.

The second ISV of the bispecific protein binds to a mucin protein, e.g. a mucin protein present on ocular, nasopharyngeal, tracheal and/or oral surfaces of a mammal. Target mucin proteins that find use in present disclosure, include without limitation, human MUC2, human MUC5AC, human MUC5B, human MUC1, human MUC4, human MUC11, mouse MUC2, mouse MUC5AC, mouse MUC5B, MUC1, mouse MUC4, mouse MUC11, hamster MUC2, hamster MUC5AC, hamster MUC5B, hamster MUC1, hamster MUC4, hamster MUC11, etc. In an embodiment, the second ISV of the bispecific protein binds to human MUC5AC protein, for example binding to a polypeptide sequence shown in FIG. 2. In some embodiments the ISV cross-reacts with human MUC5B protein.

The first and second ISV domains of the bispecific protein are joined through a protease resistant, flexible, polypeptide linker, particularly a polypeptide resistant to proteases found in mucus, e.g. serine proteases such as chymases, elastases, tryptases, asp-ases, and met-ases. In some embodiments the polypeptide linker is from about 8 to about 30 amino acids in length, e.g. from about 10 to about 30, from about 12 to about 30, from about 15 to 30; from about 15-25, from about 15 50 20 amino acids and is comprised of a poly-(gly-ser) sequence.

In some embodiments, a first ISV specifically binds to SARS-CoV2 spike protein. In some such embodiments, the first ISV specifically binds to the polypeptide of SEQ ID NO:1. Exemplary ISV sequences for this purpose include, for example, those having the amino acid sequence of any of SEQ ID NO:11; SEQ ID NO:15; SEQ ID NO:19; SEQ ID NO:23; SEQ ID NO:27; SEQ ID NO:31; SEQ ID NO:35; SEQ ID NO:39; SEQ ID NO:43; SEQ ID NO:47; SEQ ID NO:51; or an ISV having the CDR1, CDR2 and CDR3 sequences thereof.

In other embodiments, a first ISV specifically binds to a SARS-CoV spike protein. In some such embodiments, the first ISV specifically binds to the polypeptide of SEQ ID NO:2. In other embodiments, a first ISV specifically binds to a MERS-CoV spike protein. In some such embodiments, the first ISV specifically binds to the polypeptide of SEQ ID NO:3. In other embodiments, a first ISV specifically binds to an influenza hemagglutinin protein. In some such embodiments, the first ISV specifically binds to the polypeptide of SEQ ID NO:4 or SEQ ID NO:5.

In some embodiments, a second ISV specifically binds to a mucin protein. In some such embodiments, the first ISV specifically binds to the polypeptide of SEQ ID NO:6; SEQ ID NO:7; SEQ ID NO:8; SEQ ID NO:9. Exemplary ISV sequences for this purpose include, for example, those binding to a human mucin protein; and having the amino acid sequence of any of SEQ ID NO:55; SEQ ID NO:59; SEQ ID NO:63; SEQ ID NO:67; SEQ ID NO:71; SEQ ID NO:75; SEQ ID NO:79; SEQ ID NO:83; or an ISV having the CDR1, CDR2 and CDR3 sequences thereof.

The bispecific protein binds to and tethers a cognate airborne infectious virus to mucosal surfaces where the virus can be inactivated, or degraded, by mucosal enzymes, while simultaneously binding to and blocking activity of the virus, e.g. by blocking a viral spike protein and preventing its association with potential receptors expressed on mucosal membrane epithelial cells. These activities reduce infection by reducing the infectivity quotient. In some embodiments, it is desirable to tether the airborne virus to a specific mucosal environment. For instance, the airborne virus may be tethered to ocular mucosa, oral mucosa, nasopharyngeal mucosa, tracheal mucosa. In some embodiments, if tethering of the airborne virus to the ocular mucosa is desired, then the second ISV of the bispecific protein may bind to MUC5AC. In some embodiments, if sequestration of the airborne virus to the oral, nasopharyngeal, or tracheal mucosa is desired then the second ISV of the bispecific protein may bind to MUC5B.

In some embodiments the bispecific protein is provided in formulation that allows for aerosol distribution. "Aerosol formulation" means an active agent described herein in a form or formulation that is suitable for aerosol, e.g. respiratory delivery. The aerosol formulation may be in a dry powder form, it may be a solution, suspension or slurry to be nebulized, or it may be in admixture with a suitable low boiling point, highly volatile propellant. It is to be understood that more than one bispecific protein and optionally other active agents or ingredients may be incorporated into the aerosolized formulation. In certain embodiments, the active agent retains more than 50% of its activity after nebulization, preferably more than 70%. In certain embodiments, the active agent retains more than 50% of its purity after nebulization, preferably more than 70%.

In some embodiments, methods are provided for tethering an airborne infectious virus to a mucosal surface for inactivation, the method comprising spraying or otherwise coating a mucosal surface, e.g. an ocular, nasopharyngeal, tracheal and/or oral surface of a mammal, at a dose effective to reduce infectivity of the airborne infectious virus when the virus contacts the mucosal surface. In some such embodiments the virus is a respiratory virus. In some embodiments the respiratory virus is a coronavirus or an influenza virus.

In some embodiments, methods are provided for reducing infection of an individual mammal during potential exposure to human airborne infectious virus, e.g. during medical and dental procedures, and other situations where close proximity to possibly infected individuals is likely. In such methods, mucosal surfaces are sprayed or otherwise coated with a bispecific protein as described herein, at a dose effective to reduce infectivity of the airborne infectious virus when the virus contacts the mucosal surface. For example, an effective dose of the bispecific protein may be applied with a nebulizer to the nasal passages prior to exposure.

The compositions and methods provided herein are an accessible, safe, and effective strategy to reduce the spreading of infectious airborne virus, including coronavirus.

BRIEF DESCRIPTION OF THE DRAWINGS

FIG. 2. The design of coronavirus-mucin bispecific nanobody. The similarity of SARS-CoV and SARS-CoV-2 spike protein is nearly 80%, particularly high in ACE2 binding residues. MUC5AC and MUC5B are primary gel-forming mucins in respiratory tract as well as in ocular and oral mucosa, and the sequence of MUC5AC antigen has 52% with MUC5B. The coronavirus-mucin bispecific nanobody is designed based on the sequence of SARS-CoV-2 spike protein and MUC5AC but also has a promising affinity to SARS-CoV and MUC5B.

5

6 gated) or indicated ISV (Alexa Fluor 647 conjugated control nanobody, M2, M16 and M17). Blue indicate DAPI which stain nucleus, red indicate MUC5AC, one of the major mucins in mucus layer. B. Western blot validation of nano-body M17 with calu-3 condition media and human nasal mucus samples.

Figure 1:
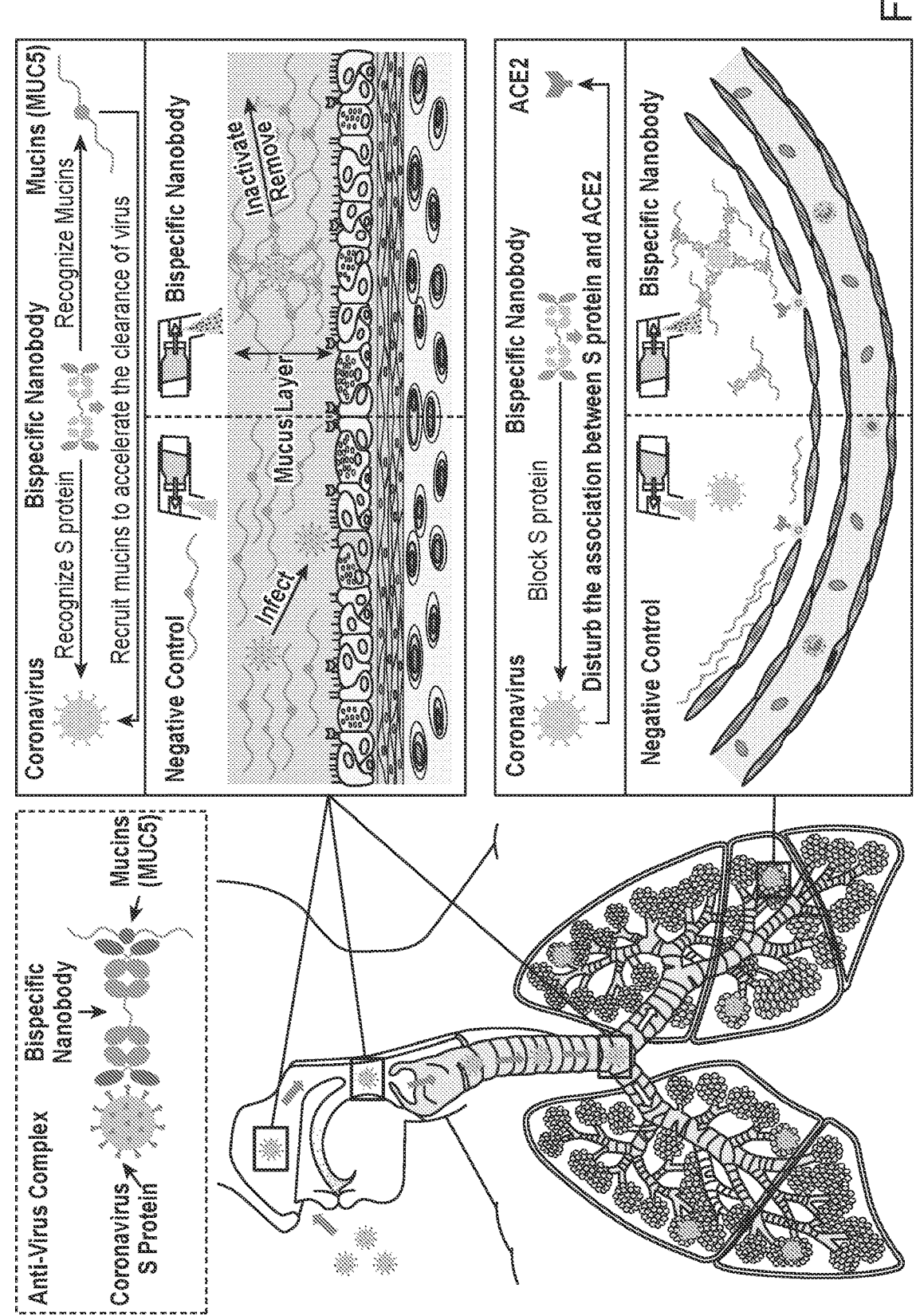
FIG. 1. The anti-coronavirus effect of coronavirus-mucin bispecific nanobody in respiratory tract. SARS-CoV receptor ACE2 are highly expressed in respiratory tract epithelial cells. In nasopharynx and trachea, bispecific nanobody will bind to coronavirus spike protein and anchor them to mucins to inactivate and remove virus. This mechanism should be effective even where the mucosal layer is thin as in the pulmonary alveolus, as the bispecific nanobody binds to the coronavirus spike protein and blocks its recognition of ACE2.
Figure 3:
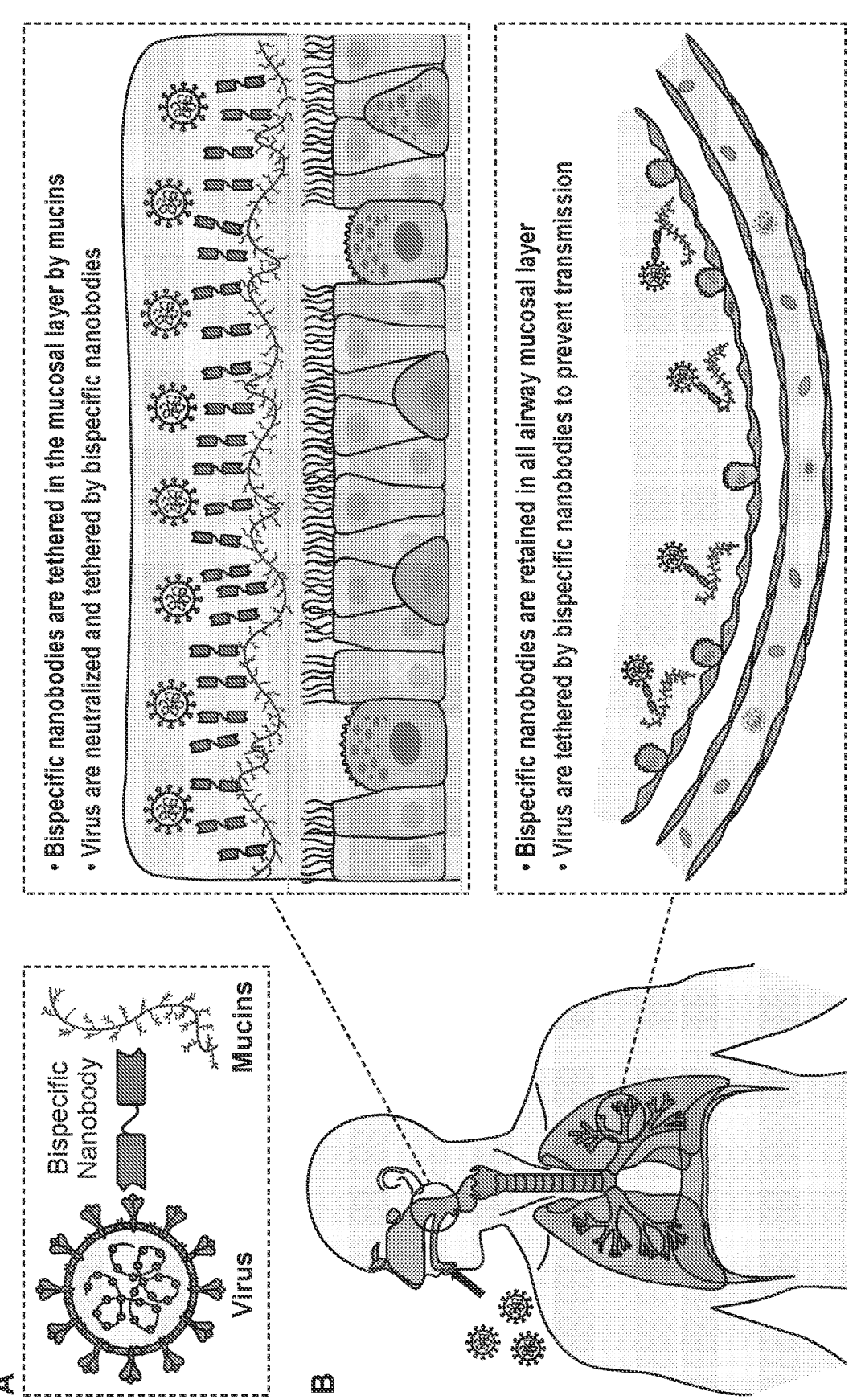
FIG. 3. Schematic diagram of mucus-tethering bispecific ISV. One portion of the bispecific nanobody specifically binds to mucins in mucus layer present on ocular, nasal, oral cavities and respiratory tract, which can tether those ISV in mucus layer to achieve higher local concentration. The second portion of the bispecific nanobody specifically binds to surface glycoproteins of airborne infectious virus, which can neutralize and physically tether those viruses to prevent infection. These two types of ISV are joined through a protease resistant linker, particularly proteases found in mucus.
Figure 4:
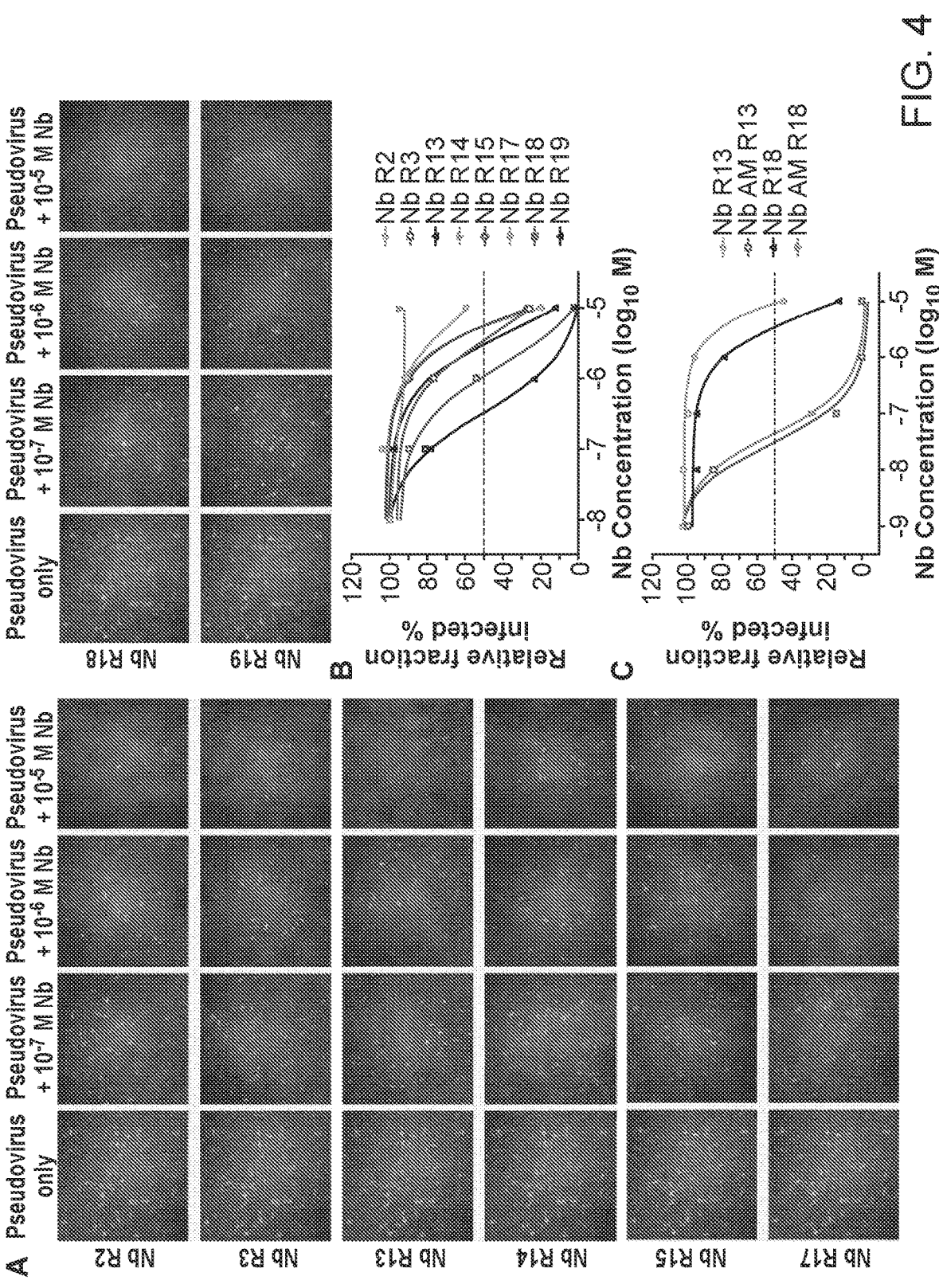
FIG. 4. Validation of SARS-CoV-2 neutralizing ISV. A. SARS-CoV-2 pseudovirus and hACE2 overexpressed HEK-293T cells were used to analysis neutralizing effect of candidate ISV. Pseudovirus were diluted in culture medium to obtain 10% infection ratio and incubated with ISV (R2, R3, R13, R14, R15, R17, R18, R19) for 1 hour at 37° C. prior to addition to hACE2-293T cells. Infected cells will express ZsGreen fluorescent protein. Images were captured 48 hours after infection. B. Flow cytometry analysis of infected cell were performed after imaging. C. Affinity maturation of nanobody R13 and R18 showed around 100 times increased neutralizing effect calculated by IC50.
Figure 5:
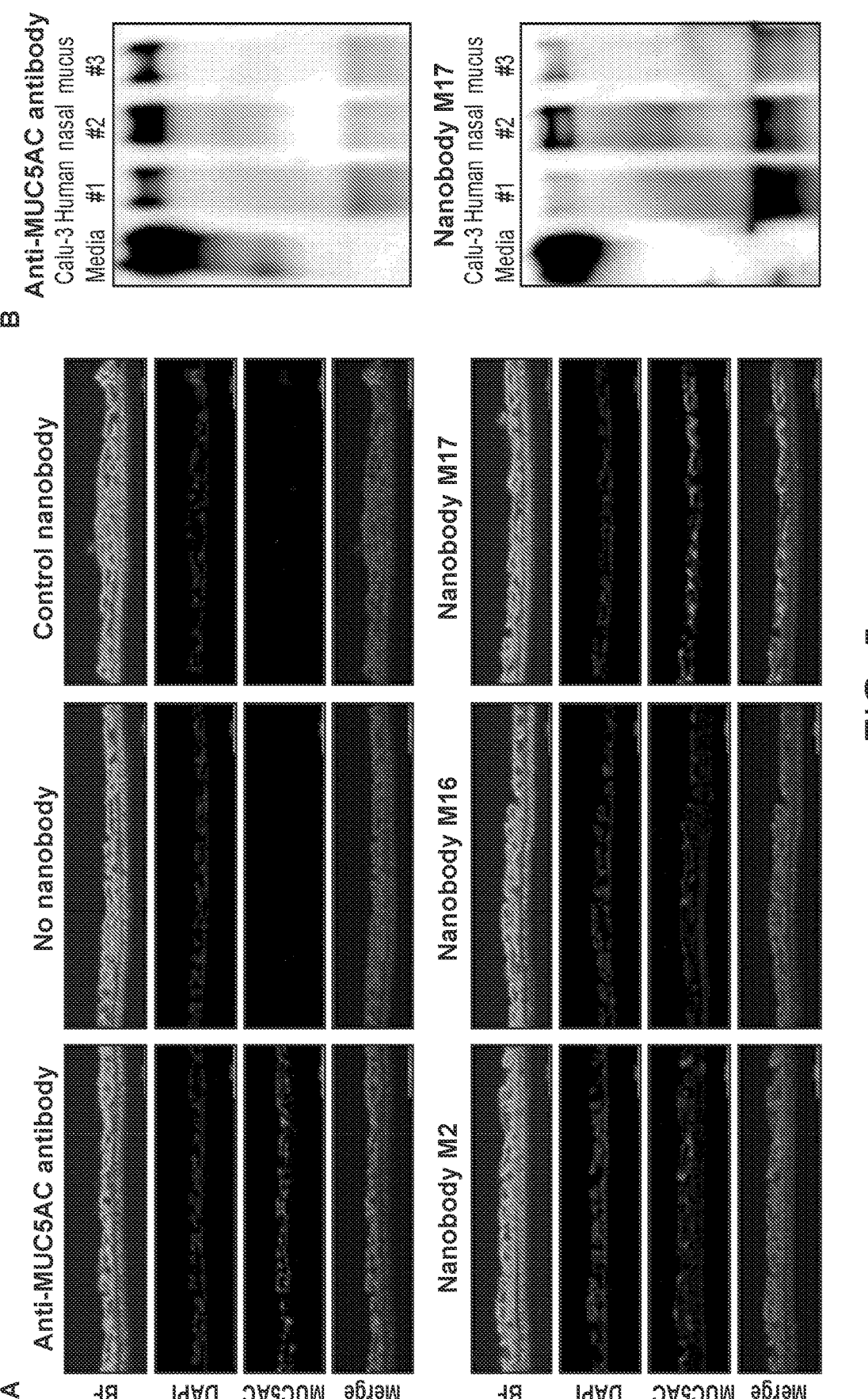
FIG. 5. Validation of MUC5AC tethering ISV. A. Mucus secreting cell line Calu-3 was used to validate mucus-tethering ISV. Sections of Calu-3 cells in transwell were stained with MUC5AC antibody (Alexa Fluor 647 conju-
Figure 6:
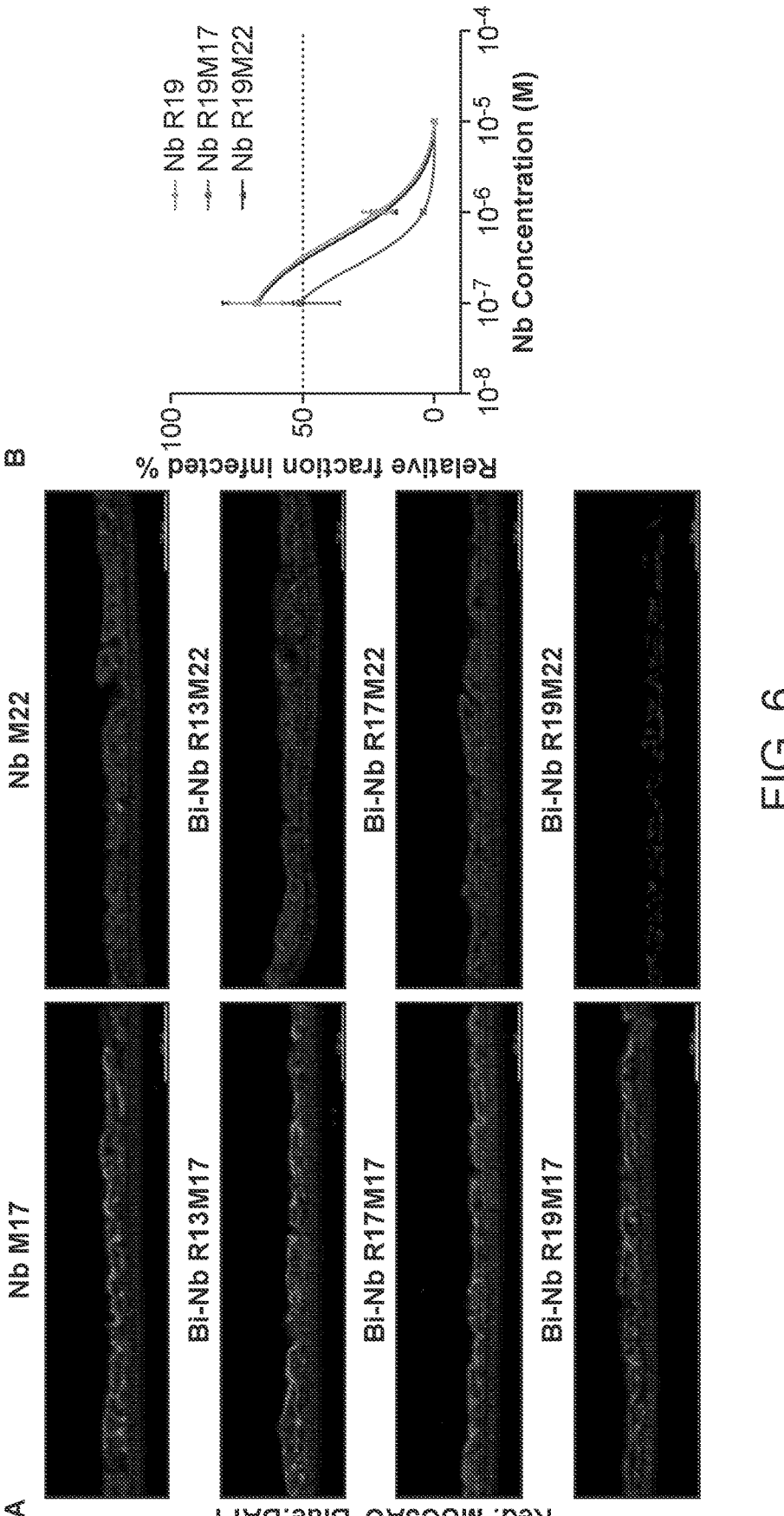

FIG. 6. Validation of mucus-tethering bispecific ISV. A. Sections of Calu-3 cells in transwell were stained with mucus-tethering ISV M17 and its bispecific version jointed with anti-SARS-CoV-2 ISV (R13, R17 and R19). M22 is negative control nanobody with poor affinity to mucin. B. Neutralization assay with mucus covered hACE2-293T cells showed higher inhibitory effect of mucus-tethering nano-body R19M17 over virus specific nanobody R19 and its bispecific version jointed with a non-mucus-tethering nano-body M22 (R19M22).

Figure 7:
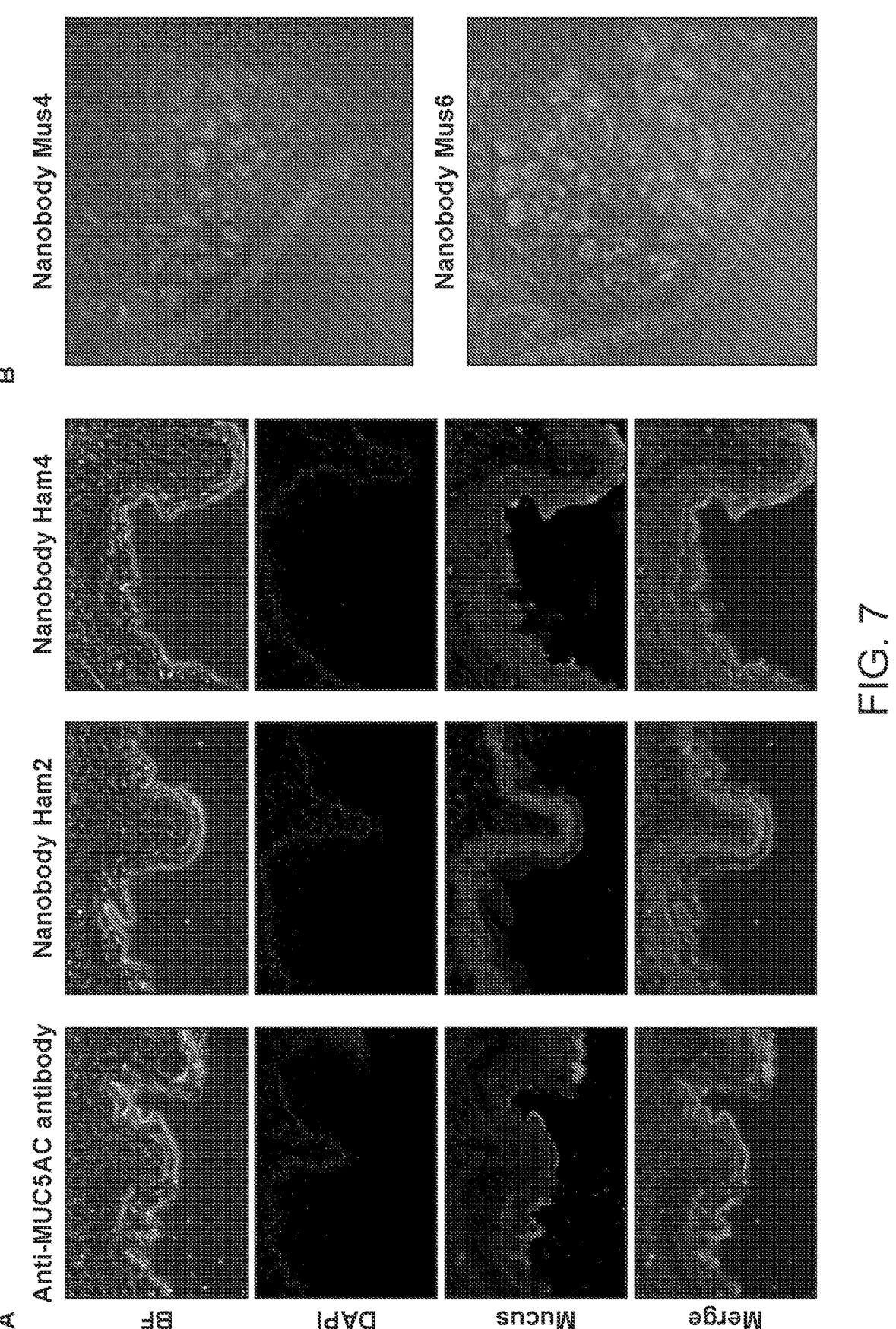

FIG. 7. Validation of hamster and mouse mucus-tethering ISV. A. Golden hamster trachea sections were stained with anti-MUC5AC antibody (Alexa Fluor 647 conjugated), nanobody candidates Ham2 and Ham28 (Alexa Fluor 647 conjugated). B. Mouse trachea sections were stained with nanobody candidates Mus4 and Mus6 (Alexa Fluor 647 conjugated). Blue indicate DAPI which stain nucleus, red indicate MUC5AC, one of the major mucins in mucus layer.

DESCRIPTION OF THE SPECIFIC EMBODIMENTS

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims. In this specification and the appended claims, the singular forms "a," "an" and "the" include plural reference unless the context clearly dictates otherwise.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the subject components of the invention that are described in the publications, which components might be used in connection with the presently described invention.

A bispecific protein is provided, comprising two different immunoglobulin "single variable domain" (ISV). As used herein, ISV is used as a general term to include but not be limited to antigen-binding domains or fragments such as variable heavy homodimer ($V_{HH}$) domains or $V_H$ or $V_L$ domains, respectively. The terms antigen-binding molecules or antigen-binding protein are used interchangeably and include also the term NANOBODIES®. A first ISV of the bispecific protein specifically binds to a surface protein found on an airborne infectious virus. Target surface proteins on airborne viruses that find use in the present disclosure, include without limitation, a SARS-CoV spike protein, a SARS-CoV2 spike protein, a MERS-CoV spike protein, Influenza A virus hemagglutinin, etc. In an embodiment, a first ISV of the bispecific protein specifically binds to a conserved domain in the spike envelope protein encoded by SARS-CoV2, exemplified by the sequence at residues 387-516 of the spike protein, and as shown in FIG. 2. The second ISV of the bispecific protein specifically binds to a mucin protein, e.g. a mucin protein present on ocular, nasopharyngeal, tracheal and/or oral surfaces of a mammal. Target mucin proteins that find use in present disclosure, include without limitation, human MUC2, human MUC5AC, human MUC5B, human MUC1, human MUC4, human MUC11, mouse MUC2, mouse MUC5AC, mouse MUC5B, mouse MUC1, mouse MUC4, mouse MUC11, hamster MUC2, hamster MUC5AC, hamster MUC5B, hamster MUC1, hamster MUC4, hamster MUC11, etc. In an embodiment, the second ISV of the bispecific protein binds to human MUC5AC protein, for example binding to a polypeptide sequence shown in FIG. 2.

The two ISV are separated by a linker, e.g. a polypeptide linker, or a non-peptidic linker, etc. The amino acid linkers that join domains can play an important role in the structure and function of multi-domain proteins. In some embodiments the linker is a flexible linker. In some embodiments, the linker moiety is a peptide linker. In some embodiments, the peptide linker comprises 8 to 30 amino acids. In some embodiments, the peptide linker comprises 8, 9, 10, 11, 12, 13, 14, 15, 16, 17, 18, 19, 20, 21, 22, 23, 24, 25, 26, 27, 28, 29, 30 amino acids. In some embodiments, the peptide linker is between 10 to 30, 15 to 30, 20 to 25, 15 to 25, etc., amino acids in length. Suitable linear peptides include poly glycine, polyserine, polyalanine and oligopeptides consisting of ala-nyl and/or serinyl and/or glycyl amino acid residues. In some embodiments, the peptide linker comprises an amino acid sequence (GGGGS)n, where n is 1, 2, 3, 4, 5, etc.; however many such linkers are known and used in the art and may serve this purpose.

In some embodiments the bispecific protein is provided in an aerosol formulation to coat exposed mucosal membranes in the eyes, nose, and mouth as well as surrounding surfaces such as seats, countertops, door handles, and belt buckles.

The bispecific protein binds to and tethers a cognate airborne infectious virus to mucosal surfaces where the virus can be inactivated, or degraded, by mucosal enzymes, while simultaneously binding to and blocking activity of the virus, e.g. by blocking a viral spike protein and preventing its association with potential receptors expressed on mucosal membrane epithelial cells. These activities reduce infection by reducing the infectivity quotient.

In some embodiments the bispecific protein is expressed in microbial cells, e.g. engineered *E. coli*, engineered *Saccharomyces cerevisiae*, etc. Microbially expressed proteins can be produced in large quantities by modifying fermentation infrastructure.

The bispecific protein formulations, e.g. aerosolized formulations, are designed to confer critical prophylaxis in the upper respiratory tract against infectious, airborne viruses, particularly respiratory viruses. For example, nasal epithelial cells express high levels of SARS-CoV-2 receptor ACE2 and are instrumental to productive infection. Compared to traditional systemically delivered neutralizing antibodies, aerosolized bispecific ISV can accumulate rapidly in respiratory tract and confer strategic protection. Furthermore, the bispecific proteins also bind to mucins, which are the primary gel forming component in mucus, thereby tethering and sequestering virus. The neutralizing effect from the binding and sequestration from mucus can effectively prevent infection and expedite viral clearance.

This will further prevent infection by reducing the infectivity quotient even if there are some viral particles that still manage to come in contact with epithelial cell surfaces. In addition, delivery with aerosolization and topical application limits entry into bloodstream and minimizes potential side effects from intravenous antibody delivery. This advantage is specific to an ISV protein, as only small, stable proteins, such as ISV, are stable enough to withstand aerosolization.

An advantage is that commercially available chemical disinfectants are effective for decontaminating the skin or contact surfaces but cannot be used directly on mucosa.

INDUSTRIAL APPLICABILITY

The compositions and methods of the invention find use in, for example, aerosolized dispersal in communal areas and semi-enclosed space (schools, shopping centers, airports); personal nebulizers for prophylactic treatment against exposure in high-risk areas (emergency rooms, clinical scenarios); as a medication to control the transmission in pulmonary alveolus; in sanitary wipes; for treatment of food products; sushi, salad bars, other food sources that may be contaminated during preparation or while serving; as an additive or in powdered form for widespread dispersal through humidifiers or air conditioning units in buildings and complexes with central air conditioning; as a topical ointment; etc.

Definitions

Immunoglobulin sequences, such as antibodies and antigen binding fragments derived there from (e.g., immunoglobulin single variable domains or ISVs) are used to specifically target their respective antigens in research and therapeutic applications. The generation of immunoglobulin single variable domains such as e.g., $V_{HH}S$ or ISV may involve selection from phage display or yeast display, for example ISV can be selected by utilizing surface display platforms where the cell or phage surface display a synthetic library of ISV, in the presence of tagged antigen. A fluorescent secondary antibody directed to the tagged antigen is added to the solution thereby labeling cells bound to antigen. Cells are then sorted using any cell sorting platform of interest e.g., magnetic-activated cell sorting (MACS) or fluorescence-activated cell sorting (FACS). Sorted clones are amplified, resulting in an enriched library of clones expressing ISV that bind antigen. The enriched library is then re-screened with antigen to further enrich for surface displayed antigen binding ISV. These clones can then be sequenced to identify the sequences of the ISV of interest and further transferred to other heterologous systems for large scale protein production.

Alternatively, similar immunoglobulin single variable domains can be generated and selected by the immunization of an experimental animal such as a llama, construction of phage libraries from immune tissue, and screening of said domains and engineered constructs thereof for the desired specificities.

Unless indicated otherwise, the term "immunoglobulin single variable domain" or "ISV" is used as a general term to include but not limited to antigen-binding domains or fragments such as $V_{HH}$ domains or $V_H$ or $V_L$ domains, respectively. $V_{HH}$ domains are of interest for the present disclosure. The terms antigen-binding molecules or antigen-binding protein are used interchangeably and include also the term NANOBODIES®. The immunoglobulin single variable domains can be light chain variable domain sequences [e.g., a $V_L$-sequence), or heavy chain variable domain sequences (e.g., a $V_H$-sequence); more specifically, they can be heavy chain variable domain sequences that are derived from a conventional four-chain antibody or heavy chain variable domain sequences that are derived from a heavy chain antibody. Accordingly, the immunoglobulin single variable domains can be single domain antibodies, or immunoglobulin sequences that are suitable for use as single domain antibodies, "dAbs", or immunoglobulin sequences that are suitable for use as dAbs, or NANOBODIES™, including but not limited to $V_{HH}$ sequences.

The invention includes immunoglobulin sequences of different origin, comprising mouse, rat, rabbit, donkey, human and camelid immunoglobulin sequences. The immunoglobulin single variable domain includes fully human, humanized, otherwise sequence optimized or chimeric immunoglobulin sequences. The immunoglobulin single variable domain and structure of an immunoglobulin single variable domain can be considered—without however being limited thereto—to be comprised of four framework regions or "FR's", which are referred to in the art and herein as "Framework region 1" or "FR1"; as "Framework region 2" or "FR2"; as "Framework region 3" or "FR3"; and as "Framework region 4" or "FR4", respectively; which framework regions are interrupted by three complementary determining regions or "CDR's", which are referred to in the art as "Complementarity Determining Region 1" or "CDR1"; as "Complementarity Determining Region 2" or "CDR2"; and as "Complementarity Determining Region 3" or "CDR3", respectively. It is noted that the terms Nanobody or Nanobodies are registered trademarks of Ablynx N.V. and thus may also be referred to as NANOBODY® or NANOBODIES®, respectively.

An amino acid sequence such as e.g. an immunoglobulin single variable domain or polypeptide according to the invention is said to be a "VHH1 type immunoglobulin single variable domain" or "VHH type 1 sequence", if said VHH1 type immunoglobulin single variable domain or VHH type 1 sequence has 85% identity (using the VHH1 consensus sequence as the query sequence and use the blast algorithm with standard setting, i.e., blosom62 scoring matrix) to the VHH1 consensus sequence and mandatorily has a cysteine in position 50, i.e., C50 (using Kabat numbering). See, for example, $V_{HH}$ domains from Camelids in the article of Riechmann and Muyldermans, J. Immunol. Methods 2000 Jun. 23; 240 (1-2): 185-195. The CDR sequences of exemplary VHH domains are disclosed, along with the relevant CDR sequences in, for example, any of SEQ ID NO: 11, 15, 19, 23, 27, 31, 35, 39, 43, 47, 51, 55, 59, 63, 67, 71, 75, 79, 83, 87, 91, 95, or 99.

The present invention relates to particular polypeptides, also referred to as "polypeptides of the invention" that comprise or essentially consist of (i) a first building block consisting essentially of a first immunoglobulin single variable domain and (ii) a second building block consisting essentially of a second immunoglobulin single variable domain, linked via a linker.

Such immunoglobulin single variable domains may be derived in any suitable manner and from any suitable source, and may for example be naturally occurring $V_{HH}$ sequences (i.e., from a suitable species of Camelid, e.g., llama) or synthetic or semi-synthetic VHs or VLs (e.g., from human). Such immunoglobulin single variable domains may include "humanized" or otherwise "sequence optimized" VHHs, "camelized" immunoglobulin sequences (and in particular camelized heavy chain variable domain sequences, i.e., camelized VHs), as well as human VHs, human VLs, camelid VHHs that have been altered by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing as further described herein.

Immunoglobulin single variable domains may comprise an amino acid sequence that corresponds to the amino acid sequence of a naturally occurring $V_{HH}$ domain, but that has been "humanized", i.e. by replacing one or more amino acid residues in the amino acid sequence of said naturally occurring $V_{HH}$ sequence (and in particular in the framework sequences) by one or more of the amino acid residues that occur at the corresponding position(s) in a $V_H$ domain from a conventional 4-chain antibody from a human being (e.g. indicated above). This can be performed in a manner known per se, which will be clear to the skilled person, for example on the basis of the further description herein and the prior art on humanization referred to herein. Again, it should be noted that such humanized immunoglobulin single variable domains of the invention can be obtained in any suitable manner known per se and thus are not strictly limited to polypeptides that have been obtained using a polypeptide that comprises a naturally occurring $V_{HH}$ domain as a starting material.

Another class of immunoglobulin single variable domains of the invention comprises immunoglobulin single variable domains with an amino acid sequence that corresponds to the amino acid sequence of a naturally occurring $V_H$ domain, but that has been "camelized", i.e. by replacing one or more amino acid residues in the amino acid sequence of a naturally occurring $V_H$ domain from a conventional 4-chain antibody by one or more of the amino acid residues that occur at the corresponding position(s) in a $V_{HH}$ domain of a heavy chain antibody. This can be performed in a manner known per se, which will be clear to the skilled person, for example on the basis of the description herein. Such "camelizing" substitutions may be inserted at amino acid positions that form and/or are present at the $V_H$-$V_L$ interface, and/or at the so-called Camelidae hallmark residues (see for example WO 94/04678 and Davies and Riechmann (1994 and 1996)). The $V_H$ sequence that is used as a starting material or starting point for generating or designing the camelized immunoglobulin single variable domains is preferably a $V_H$ sequence from a mammal, more preferably the $V_H$ sequence of a human being, such as a $V_H3$ sequence. However, it should be noted that such camelized immunoglobulin single variable domains of the invention can be obtained in any suitable manner known per se and thus are not strictly limited to polypeptides that have been obtained using a polypeptide that comprises a naturally occurring $V_H$ domain as a starting material.

The term "antibody" herein is used in the broadest sense and specifically covers monoclonal antibodies, polyclonal antibodies, monomers, dimers, multimers, multispecific antibodies (e.g., bispecific antibodies), heavy chain only antibodies, three chain antibodies, single chain Fv, single domain antibodies, ISV, etc., and also include antibody fragments with or without pegylation, so long as they exhibit the desired biological activity (Miller et al (2003) Jour. of Immunology 170:4854-4861).

A "functional" or "biologically active" antibody or antigen-binding molecule is one capable of exerting one or more of its natural activities in structural, regulatory, biochemical or biophysical events. For example, a functional antibody or other binding molecule may have the ability to specifically bind an antigen and the binding may in turn elicit or alter a cellular or molecular event such as signaling transduction or phagocytosis. A functional antibody may also block ligand activation of a receptor or act as an agonist or antagonist or as an allosteric modulator.

The term antibody may reference a full-length heavy chain, a full length light chain, an intact immunoglobulin molecule; or an immunologically active portion of any of these polypeptides, i.e., a polypeptide that comprises an antigen binding site that immunospecifically binds an antigen of a target of interest or part thereof.

The term "hypervariable region" when used herein refers to the amino acid residues of an antibody which are responsible for antigen-binding. The hypervariable region may comprise amino acid residues from a "complementarity determining region" or "CDR", and/or those residues from a "hypervariable loop". "Framework Region" or "FR" residues are those variable domain residues other than the hypervariable region residues as herein defined.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations, which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method.

"Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules; ISV or domain antibodies comprising single Ig domains from human or non-human species or other specific single-domain binding modules including non-antibody binding proteins such as, but not limited to, adnectins and anticalins; and multispecific or multivalent structures formed from antibody fragments.

The term "NANOBODY®" as used herein refers to a single domain antibody consisting of a single monomeric variable domain (also referred to as a variable heavy homodimer [$V_{HH}$] domain). The single domain antibodies are naturally produced by animals belonging to the camelid family. Nanobodies are smaller than human antibodies, where ISV are generally 12-15 kDa, human antibodies are generally 150-160 kDa, Fab fragments are ~50 kDa and single-chain variable fragments are ~25 kDa. NANOBOD-IES® provide specific advantages over traditional antibodies including smaller sizes, they are more easily engineered, higher chemical and thermo stability, better solubility, deeper tissue penetration, the ability to bind small cavities and difficult to access epitopes of target proteins, the ability to manufacture in microbial cells (i.e. cheaper production costs relative to animal immunization), and the like.

"Aerosol composition" or "aerosol formulation" means an active agent described herein in a form or formulation that is suitable for pulmonary delivery. The aerosol composition may be in the dry powder form, it may be a solution, suspension or slurry to be nebulized, or it may be in admixture with a suitable low boiling point, highly volatile propellant. It is to be understood that more than one bispecific protein and optionally other active agents or ingredients may be incorporated into the aerosolized formulation or aerosol composition and that the use of the term "bispecific protein" or "active agent" in no way excludes the use of two or more such proteins or other agents or ingredients.

Active agent formulations suitable for use in the present application include dry powders, solutions, suspensions or slurries for nebulization and particles suspended or dissolved within a propellant. Dry powders suitable for use in the present application include amorphous active agents, crystalline active agents and mixtures of both amorphous and crystalline active agents. The dry powder active agents have a particle size selected to permit penetration into the alveoli of the lungs, that is, preferably 10 μm mass median diameter $(MMD)_5$ preferably less than 7.5 μm, and most preferably less than 5 μm, and usually being in the range of 0.1 μm to 5 μm in diameter. The delivered dose efficiency (DDE) of these powders is >30%, usually >40%, preferably >50 and often >60% and the aerosol particle size distribution is about 1.0-5.0 μm mass median aerodynamic diameter (MMAD), usually 1.5-4.5 μm MMAD and preferably 1.5-4.0 μm MMAD. These dry powder active agents have a moisture content below about 10% by weight, usually below about 5% by weight, and preferably below about 3% by weight. Such active agent powders are described in WO 95/24183 and WO 96/32149, which are incorporated by reference herein.

Dry powder active agent formulations are preferably prepared by spray drying under conditions which result in a substantially amorphous powder. Bulk active agent, usually in crystalline form, is dissolved in a physiologically acceptable aqueous buffer, typically a citrate buffer having a pH range from about 2 to 9. The active agent is dissolved at a concentration from 0.01% by weight to 1% by weight, usually from 0.1% to 0.2%. The solutions may then be spray dried in a conventional spray drier available from commercial suppliers such as Niro A/S (Denmark), Buchi (Switzerland) and the like, resulting in a substantially amorphous powder. These amorphous powders may also be prepared by lyophilization, vacuum drying, or evaporative drying of a suitable active agent solution under conditions to produce the amorphous structure. The amorphous active agent formulation so produced can be ground or milled to produce particles within the desired size range. Dry powder active agents may also be in a crystalline form. The crystalline dry powders may be prepared by grinding or jet milling the bulk crystalline active agent. The active agent powders of the present application may optionally be combined with pharmaceutical carriers or excipients which are suitable for respiratory and pulmonary administration. Such carriers may serve simply as bulking agents when it is desired to reduce the active agent concentration in the powder which is being delivered to a patient, but may also serve to improve the dispersability of the powder within a powder dispersion device in order to provide more efficient and reproducible delivery of the active agent and to improve handling characteristics of the active agent such as flowability and consistency to facilitate manufacturing and powder filling. Such excipients include but are not limited to (a) carbohydrates, e.g., monosaccharides such as fructose, galactose, glucose, D-mannose, sorbose, and the like; disaccharides, such as lactose, trehalose, cellobiose, and the like; cyclodextrins, such as 2-hydroxypropyl-.beta.-cyclodextrin; and polysaccharides, such as raffmose, maltodextrins, dextrans, and the like; (b) amino acids, such as glycine, arginine, aspartic acid, glutamic acid, cysteine, lysine, and the like; (c) organic salts prepared from organic acids and bases, such as sodium citrate, sodium ascorbate, magnesium gluconate, sodium gluconate, tromethamin hydrochloride, and the like; (d) peptides and proteins such as aspartame, human serum albumin, gelatin, and the like; and (e) alditols, such as mannitol, xylitol, and the like. A preferred group of carriers includes lactose, trehalose, raffmose, maltodextrins, glycine, sodium citrate, human serum albumin and mannitol.

The dry powder active agent formulations may be delivered using Inhale Therapeutic Systems' dry powder inhaler as described in WO 96/09085 which is incorporated herein by reference, but adapted to control the flow rate at a desirable level or within a suitable range. The dry powders may also be delivered using a metered dose inhaler as described by Laube et al. in U.S. Pat. No. 5,320,094, which is incorporated by reference herein. Nebulized solutions may be prepared by aerosolizing commercially available active agent formulation solutions. These solutions may be delivered by a jet nebulizer such as the Raindrop, produced by Puritan Bennett, the use of which is described by Laube et al., supra. Other methods for delivery of solutions, suspensions of slurries are described by Rubsamen et al, U.S. Pat. No. 5,672,581. A device that uses a vibrating, piezoelectric member is described in Ivri et al., U.S. Pat. No. 5,586,550, which is incorporated by reference herein.

Propellant systems may include an active agent dissolved in a propellant or particles suspended in a propellant. Both of these types of formulations are described in Rubsamen et al., U.S. Pat. No. 5,672,581, which is incorporated herein by reference. In certain embodiments, an aerosol or nebulization nanobody composition can be combined with one or more other aerosol or nebulization treatments, such as sympathomimetics (e.g., albuterol), antibiotics (e.g., tobramycin), deoxyribonucleases (e.g., pulmozyme), anticholinergic drugs (e.g., ipratropium bromide), or corticosteroids.

In certain embodiments, an aerosol or nebulization bispecific protein composition can be combined with one or more other therapies (concurrently or sequentially) administered via nebulization, inhalation, intravenous or oral routes, such as nucleoside analogs, cytokines or cytokine blocking agents, protease inhibitors, etc.

A bispecific protein may be formulated as microparticles. Microparticles having a diameter of between 0.5 and 10 microns can penetrate the lungs, passing through most of the natural barriers. A diameter of less than ten microns is generally required to bypass the throat; a diameter of 0.5 microns or greater is usually required to avoid being exhaled.

In certain embodiments, the subject bispecific protein or therapeutic is formulated in a supramolecular complex, which may have a diameter of between 0.5 and 10 microns, which can be aggregated into particles having a diameter of between 0.5 and 10 microns.

In other embodiments, the subject therapeutics are provided in liposomes or supramolecular complexes appropriately formulated for pulmonary delivery. In addition to the supramolecular complexes, a number of other polymers can be used to form microparticles. As used herein, the term "microparticles" includes microspheres (uniform spheres), microcapsules (having a core and an outer layer of polymer), and particles of irregular shape.

Polymers are preferably biodegradable within the time period over which release of the nanobody or therapeutic is desired or relatively soon thereafter, generally in the range of one year, more typically a few months, even more typically a few days to a few weeks. Biodegradation can refer to either a breakup of the microparticle, that is, dissociation of the polymers forming the microparticles and/or of the polymers themselves. This can occur as a result of change in pH from the carrier in which the particles are administered to the pH at the site of release, as in the case of the diketopiperazines, hydrolysis, as in the case of poly (hydroxy acids), by diffusion of an ion such as calcium out of the microparticle, as in the case of microparticles formed by ionic bonding of a polymer such as alginate, and by enzymatic action, as in the case of many of the polysaccharides and proteins. In some cases, linear release may be most useful, although in others a pulse release or "bulk release" may provide more effective results.

Representative synthetic materials are: diketopiperazines, poly(hydroxy acids) such as poly(lactic acid), poly(glycolic acid) and copolymers thereof, polyanhydrides, polyesters such as polyorthoesters, polyamides, polycarbonates, polyalkylenes such as polyethylene, polypropylene, poly(ethylene glycol), poly(ethylene oxide), poly(ethylene terephthalate), poly vinyl compounds such as polyvinyl alcohols, polyvinyl ethers, polyvinyl esters, polyvinyl halides, polyvinylpyrrolidone, polyvinylacetate, and poly vinyl chloride, polystyrene, polysiloxanes, polymers of acrylic and methacrylic acids including poly(methyl methacrylate), poly (ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyurethanes and copolymers thereof, celluloses including alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellullose triacetate, and cellulose sulphate sodium salt, poly(butic acid), poly(valeric acid), and poly(lactide-co-caprolactone).

Natural polymers include alginate and other polysaccharides including dextran and cellulose, collagen, albumin and other hydrophilic proteins, zein and other prolamines and hydrophobic proteins, copolymers and mixtures thereof. As used herein, chemical derivatives thereof refer to substitutions, additions of chemical groups, for example, alkyl, alkylene, hydroxylations, oxidations, and other modifications in the art. Bioadhesive polymers include bioerodible hydrogels described by H. S. Sawhney, C. P. Pathak and J. A. Hubell in Macromolecules, 1993, 26, 581-587, polyhyaluronic acids, casein, gelatin, gluten, polyanhydrides, polyacrylic acid, alginate, chitosan, and polyacrylates.

To further illustrate, the matrices can be formed of the polymers by solvent evaporation, spray drying, solvent extraction and other methods known to those skilled in the art. Methods developed for making microspheres for drug delivery are described in the literature, for example, as described by Mathiowitz and Langer, J. Controlled Release 5, 13-22 (1987); Mathiowitz, et al., Reactive Polymers 6, 275-283 (1987); and Mathiowitz, et al., J. Appl. Polymer Sci. 35, 755-774 (1988). The selection of the method depends on the polymer selection, the size, external morphology, and crystallinity that is desired, as described, for example, by Mathiowitz, et al., Scanning Microscopy 4, 329-340 (1990); Mathiowitz, et al., J. Appl. Polymer Sci. 45, 125-134 (1992); and Benita, et al., J. Pharm. Sci. 73, 1721-1724 (1984). In solvent evaporation, described for example, in Mathiowitz, et al., (1990), Benita, and U.S. Pat. No. 4,272,398 to Jaffe, the polymer is dissolved in a volatile organic solvent. The nanobody and/or therapeutic, either in soluble form or dispersed as fine particles, is added to the polymer solution, and the mixture is suspended in an aqueous phase that contains a surface active agent such as poly(vinyl alcohol). The resulting emulsion is stirred until most of the organic solvent evaporates, leaving solid microspheres.

The term "biological sample" encompasses a variety of sample types obtained from an organism and can be used in a diagnostic or monitoring assay. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples.

The terms "polypeptide," "peptide" and "protein" are used interchangeably herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, i.e., an .alpha. carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The terms "subject," "individual," and "patient" are used interchangeably herein to refer to a mammal being assessed for treatment and/or being treated. In an embodiment, the mammal is a human. The terms "subject," "individual," and "patient" encompass, without limitation, individuals susceptible to coronavirus infection. Subjects may be human, but also include other mammals, particularly those mammals useful as laboratory models for human disease, e.g. mouse, rat, etc. Also included are mammals such as domestic and other species of canines, felines, and the like.

The term "diagnosis" is used herein to refer to the identification of a molecular or pathological state, disease or condition.

The term "prognosis" is used herein to refer to the prediction of the likelihood of disease-attributable death or progression. The term "prediction" is used herein to refer to the act of foretelling or estimating, based on observation, experience, or scientific reasoning. In one example, a physician may predict the likelihood that a patient will survive, following therapy.

As used herein, the terms "treatment," "treating," and the like, refer to administering an agent, or carrying out a procedure, for the purposes of obtaining an effect. The effect may be prophylactic in terms of completely or partially preventing a disease, e.g. infection, or symptom thereof and/or may be therapeutic in terms of effecting a partial or complete cure for a disease and/or symptoms of the disease.

Treating may refer to any indicia of success in the treatment or amelioration or prevention of disease, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the present invention to prevent or delay, to alleviate, or to arrest or inhibit development of the symptoms or conditions. The term "therapeutic effect" refers to the reduction, elimination, or prevention of the disease, symptoms of the disease, or side effects of the disease in the subject.

"In combination with", "combination therapy" and "combination products" refer, in certain embodiments, to the concurrent administration to a patient of a first therapeutic and the compounds as used herein. When administered in combination, each component can be administered at the same time or sequentially in any order at different points in time. Thus, each component can be administered separately but sufficiently closely in time so as to provide the desired therapeutic effect.

As used herein, the term "correlates," or "correlates with," and like terms, refers to a statistical association between instances of two events, where events include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases.

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" means salts and esters that are pharmaceutically acceptable and have the desired pharmacological properties. Such salts include salts that can be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g., ethanolamine, diethanolamine, triethanolamine, tromethamine, N methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g., $C_{1-6}$ alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters. Also, certain compounds named in this invention may be present in more than one stereoisomeric form, and the naming of such compounds is intended to include all single stereoisomers and all mixtures (whether racemic or otherwise) of such stereoisomers.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

As used in this disclosure, the term "epitope" means any antigenic determinant on an antigen to which the paratope of an antibody (ISV) binds. Epitopic determinants usually consist of chemically active surface groupings of molecules such as amino acids or sugar side chains and usually have specific three dimensional structural characteristics, as well as specific charge characteristics.

The word "label" when used herein refers to a detectable compound or composition which is conjugated directly or indirectly to the binding protein. The label may itself be detectable by itself (directly detectable label) (e.g., radio-isotope labels or fluorescent labels) or, or the label can be indirectly detectable, e.g., in the case of an enzymatic label, the enzyme may catalyze a chemical alteration of a substrate compound or composition and the product of the reaction is detectable.

As used herein, the term "correlates," or "correlates with," and like terms, refers to a statistical association between instances of two events, where events include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases.

Methods of Treatment

In one respect, this application is directed to pulmonary delivery compositions and/or devices for delivering a bis-pecific ISV protein to the respiratory system. The respiratory tract includes the upper airways, including the oropharynx and larynx, followed by the lower airways, which include the trachea followed by bifurcations into the bronchi and bronchioli. The upper and lower airways are called the conductive airways. The terminal bronchioli then divide into respiratory bronchioli which then lead to the ultimate respiratory zone, the alveoli, or deep lung.

Pulmonary drug delivery may be achieved by inhalation, and administration by inhalation herein may be oral and/or nasal. Examples of pharmaceutical devices for pulmonary delivery include metered dose inhalers (MDIs), dry powder inhalers (DPIs), and nebulizers. Exemplary delivery systems by inhalation which can be adapted for delivery of the subject antibody and/or active agent are described in, for example, U.S. Pat. Nos. 5,756,353; 5,858,784; and PCT applications WO98/31346; WO98/10796; WO00/27359; WO01/54664; WO02/060412. Other aerosol formulations that may be used for delivering the antibody and/or active agent are described in U.S. Pat. Nos. 6,294,153; 6,344,194; 6,071,497, and PCT applications WO02/066078; WO02/053190; WOO 1/60420; WO00/66206.

Pressurized metered dose inhalers (pMDIs) are the most commonly used inhaler worldwide. The aerosol is created when a valve is opened (usually by pressing down on the propellant canister), allowing liquid propellant to spray out of a canister. Typically, a drug or therapeutic is contained in small particles (usually a few microns in diameter) suspended in the liquid propellant, but in some formulations the drug or therapeutic may be dissolved in the propellant. The propellant evaporates rapidly as the aerosol leaves the device, resulting in small drug or therapeutic particles that are inhaled. Propellants typically used in such pMDIs include but are not limited to hydrofluoroalkanes (HFAs). A surfactant may also be used, for example, to formulate the drug or therapeutic, with pMDIs. Other solvents or excipients may also be employed with pMDIs, such as ethanol, ascorbic acid, sodium metabisulfate, glycerin, chlorobutanol, and cetylpyridium chloride. Such pMDIs may further include add-on devices such as, for example, spacers, holding chambers and other modifications.

Nebulizers produce a mist of drug-containing liquid droplets for inhalation. They are usually classified into two types: ultrasonic nebulizers and jet nebulizers. Single breath atomizers have also been developed (e.g., Respimat®), which is used to deliver a drug in a single inhalation and may be preferred because of less contamination. Jet nebulizers are more common and use a source of pressurized air to blast a stream of air through a drug-containing water reservoir, producing droplets in a complex process involving a vis-cosity-induced surface instability that leads to nonlinear phenomena in which surface tension and droplet breakup on baffles play a role. Ultrasonic nebulizers produce droplets by mechanical vibration of a plate or mesh. In either type of nebulizer, the drug is usually contained in solution in the liquid in the nebulizer and so the droplets being produced contain drug in solution. However, for some formulations (e.g., Pulmicort) the drug is contained in small particles suspended in the water, which are then contained as particles suspended inside the droplets being produced. Certain excipients are usually included in formulations suitable for nebulization, such as sodium chloride (e.g., to maintain isotonicity), mineral acids and bases (e.g., to maintain or adjust pH), nitrogen headspace sparging, benzalkonium chloride, calcium chloride, sodium citrate, disodium edtate, and polysorbate 80.

The third type of inhaler is the dry powder inhaler (DPI). In DPIs, the aerosol is usually a powder, contained within the device until it is inhaled. The therapeutic or drug is manufactured in powder form as small powder particles (usually a few millionths of a meter, or micrometers, in diameter). In many DPIs, the drug or therapeutic is mixed with much larger sugar particles (e.g., lactose monohydrate), that are typically 50-100 micrometers in diameter. The increased aerodynamic forces on the lactose/drug agglomerates improve entrainment of the drug particles upon inhalation, in addition to allowing easier filling of small individual powder doses. Upon inhalation, the powder is broken up into its constituent particles with the aid of turbulence and/or mechanical devices such as screens or spinning surfaces on which particle agglomerates impact, releasing the small, individual drug powder particles into the air to be inhaled into the lung. The sugar particles are usually intended to be left behind in the device and/or in the mouth-throat.

A further aspect of the invention provides a biopharmaceutical package comprising a bispecific protein as described herein and a nebulizer, wherein the package is suitable for preventing respiratory infection by a virus. The biopharmaceutical package may further comprise an active agent in addition to the antibody. The biopharmaceutical package may also comprise instructions for use.

An example of formulation suitable for aerosolization or nebulization of a bispecific protein is in physiologic. osmolarity (e.g., between 280 and 320 mM) at a suitable pH (e.g., pH 6 to 8). A formulation of the present application may further comprise an excipient, for example polysorbate 80 which can be used at 0.0015 to 0.02%.

Methods of preparing these formulations or compositions include the step of bringing into association a compound of the present application with the carrier and, optionally, one or more accessory ingredients. In general, the formulations are prepared by uniformly and intimately bringing into association a compound of the present application with liquid carriers, or finely divided solid carriers, or both, and then, if necessary, shaping the product.

The effect of treatment can be prophylactic in terms of completely or partially preventing infection. Those in need of treatment include those already inflicted (e.g., those with infection, those with an infection, etc.) as well as those in which prevention is desired (e.g., those with increased susceptibility to infection, those with an increased likelihood of infection, those suspected of having infection, those suspected of harboring an infection, etc.).

A therapeutic treatment is one in which the subject is inflicted prior to administration and a prophylactic treatment is one in which the subject is not inflicted prior to administration. In some embodiments, the subject has an increased likelihood of becoming inflicted or is suspected of being inflicted prior to treatment. In some embodiments, the subject is suspected of having an increased likelihood of becoming inflicted.

As used herein, the term "infection" refers to any state in at least one cell of an organism (i.e., a subject) is infected by a virus. As used herein, the term "infectious agent" refers to a foreign biological entity, particularly an airborne infectious respiratory virus including, for example, coronaviruses such as SARS-CoV; SARS-COV2; MERS-CoV; influenza virus; etc.

SARS-CoV-2 is an enveloped β-coronavirus, with a genetic sequence very similar to SARS-CoV-1 (80%) and bat coronavirus RaTG13 (96.2%). The viral envelope is coated by spike (S) glycoprotein, envelope (E), and membrane (M) proteins. Host cell binding and entry are mediated by the S protein. The first step in infection is virus binding to a host cell through its target receptor. The S1 sub-unit of the S protein contains the receptor binding domain that binds to the peptidase domain of angiotensin-converting enzyme 2 (ACE 2). In SARS-CoV-2 the S2 sub-unit is highly preserved and is considered a potential antiviral target.

The terms "co-administration", "co-administer", and "in combination with" include the administration of two or more therapeutic agents (e.g., a blocking agent and a nucleotide/nucleoside analog) either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent. Administration may be combined with co-administration of agents preventing re-infection of new cells, siRNAs targeting virus sequences, immunodulator (TLR agonists, etc), RT or polymerase inhibitor, therapeutic vaccines, and the like.

Treatment may also be combined with other active agents, such as antibiotics, cytokines, anti-viral agents, etc. Classes of antibiotics include penicillins, e.g. penicillin G, penicillin V, methicillin, oxacillin, carbenicillin, nafcillin, ampicillin, etc.; penicillins in combination with β-lactamase inhibitors, cephalosporins, e.g. cefaclor, cefazolin, cefuroxime, moxalactam, etc.; carbapenems; monobactams; aminoglycosides; tetracyclines; macrolides; lincomycins; polymyxins; sulfonamides; quinolones; chloramphenical; metronidazole; spectinomycin; trimethoprim; vancomycin; etc. Cytokines may also be included, e.g. interferon γ, tumor necrosis factor α, interleukin 12, etc. Antiviral agents may also be used in treatment.

A "therapeutically effective dose" or "therapeutic dose" is an amount sufficient to effect desired clinical results (i.e., achieve therapeutic efficacy). A therapeutically effective dose can be administered in one or more administrations. In some embodiments the bispecific protein is administered at a dose of less than 20 mg/kg body weight, less than 10 mg/kg, less than 5 mg/kg, less than 1 mg/kg, less than 0.5 mg/kg, less than 0.25 mg/kg, less than 0.1 mg/kg, less than 0.5 mg/kg, less than 0.1 mg/kg. The therapeutic dose may be, for example, from 0.1 to 5 mg/kg, from 0.25 to 5 mg/kg, from 0.5 to 5 mg/kg, from 0.75 to 5 mg/kg, from 1 to 5 mg/kg; or from 0.1 to 2.5 mg/kg, from 0.25 to 2.5 mg/kg, from 0.5 to 2.5 mg/kg, from 0.7 to 2.5 mg/kg; from 0.1 to 1 mg/kg, from 0.25 to 1 mg/kg, from 0.5 to 1 mg/kg, from 0.75 to 1 mg/kg, etc.

Dosage and frequency may vary depending on the half-life of the agent. It will be understood by one of skill in the art that such guidelines will be adjusted for the molecular weight of the active agent, e.g. in the use of antibody fragments, in the use of antibody conjugates, etc. The dosage may also be varied for localized administration, e.g. intranasal, inhalation, etc., or for systemic administration, e.g. i.m., i.p., i.v., s.c., and the like.

Toxicity of the agents can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in further optimizing and/or defining a therapeutic dosage range and/or a sub-therapeutic dosage range (e.g., for use in humans). The exact formulation, route of administration and dosage can be chosen by the individual physician in view of the patient's condition.

Bispecific ISV Proteins

In one respect, this application is directed to bispecific ISV proteins to sequester airborne viruses to mucosal surfaces. Bispecific proteins are composed of two ISV domains joined by a flexible linker. The first ISV domain of the bispecific protein binds to a surface expressed protein found on the airborne virus. The second ISV domain of the bispecific protein binds to a mucin. Collectively, the first ISV domain binds to an airborne virus which when it comes in contact with a mucosal surface the airborne virus is then tethered to said mucosal surface through the second ISV domain of the bispecific protein. Upon tethering, enzymes found within the mucosa degrade the airborne virus thereby inactivating it.

First and second ISV domains may be generated using any suitable method. Suitable methods for the generation and screening of ISVs include without limitation, immunization of dromedaries, immunization of camels, immunization of alpacas, immunization of sharks, yeast surface display, etc. Yeast surface display has been successfully used to generate specific ISVs as shown in McMahon et al. (2018) Nature Structural Molecular Biology 25(3): 289-296 which is specifically incorporated herein by reference.

In some embodiments, a first ISV specifically binds to SARS-CoV2 spike protein. In some such embodiments, the first ISV specifically binds to the polypeptide of SEQ ID NO:1. Exemplary ISV sequences for this purpose include, for example, those having the amino acid sequence of any of SEQ ID NO:11; SEQ ID NO:15; SEQ ID NO:19; SEQ ID NO:23; SEQ ID NO:27; SEQ ID NO:31; SEQ ID NO:35; SEQ ID NO:39; SEQ ID NO:43; SEQ ID NO:47; SEQ ID NO:51; or an ISV having the CDR1, CDR2 and CDR3 sequences thereof.

In other embodiments, a first ISV specifically binds to a SARS-CoV spike protein. In some such embodiments, the first ISV specifically binds to the polypeptide of SEQ ID NO:2. In other embodiments, a first ISV specifically binds to a MERS-CoV spike protein. In some such embodiments, the first ISV specifically binds to the polypeptide of SEQ ID NO:3. In other embodiments, a first ISV specifically binds to an influenza hemagglutinin protein. In some such embodiments, the first ISV specifically binds to the polypeptide of SEQ ID NO:4 or SEQ ID NO:5.

In some embodiments, a second ISV specifically binds to a mucin protein. In some such embodiments, the first ISV specifically binds to the polypeptide of SEQ ID NO:6; SEQ ID NO:7; SEQ ID NO:8; SEQ ID NO:9. Exemplary ISV sequences for this purpose include, for example, those binding to a human mucin protein; and having the amino acid sequence of any of SEQ ID NO:55; SEQ ID NO:59; SEQ ID NO:63; SEQ ID NO:67; SEQ ID NO:71; SEQ ID NO:75; SEQ ID NO:79; SEQ ID NO:83; or an ISV having the CDR1, CDR2 and CDR3 sequences thereof.

Mucin proteins may be targeted by a bispecific protein to not only tether an infectious airborne virus, but may also act to reduce the penetration of bispecific proteins in the blood or other tissues. A reduction in penetration may be desired in order to limit side effects resulting from bispecific protein function outside mucosal surfaces. The targeting of mucins may also allow for increased stability and residency time of bispecific proteins on mucosal surfaces.

The amino acid sequence of target antigens that find use in the present disclosure include without limitation, the sequence to a SARS-CoV spike protein, the sequence to a SARS-CoV2 spike protein, the sequence to a MERS-CoV spike protein, the sequence to Influenza A virus hemagglutinin, etc. An exemplary amino acid sequence to use to generate a first ISV domain directed to SARS-CoV2 spike protein may comprise the amino acid sequence: RVQPTE-SIVRFPNITNLCPFGEVFNATRFASVYAWNRKRISNC-VADYSVLYNSASFSTFKCYGV SPTKLNDLCFTNVY-ADSFVIRGDEVRQIAPGQTGKIADYNYKLPDD-FTGCVIAWNSNNLDSKVG GNYNYLYRL-FRKSNLKPFERDISTEIYQAGSTPCNGVEGFN-CYFPLQSYGFQPTNGVGYQPYR VVVLSFELL-HAPATVCGPKKSTNLVKNKCVNF (SEQ ID NO:1). In some embodiments, the target amino acid sequence used to generate the first ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO:1.

An exemplary amino acid sequence to use to generate a first ISV domain directed to SARS-CoV spike protein may comprise the amino acid sequence: RVVPSGDVVRFPNITNLCPF-GEVFNATKFPSVYAWERKKISNCVADYSVLYNSTFF-STFKCYGV SATKLNDLCFSNVY-ADSFVVKGDDVRQIAPGQTGVIADYNYKLPD-DFMGCVLAWNTRNIDATS TGNYNYKYRYLRHGKLRPFERDIS-NVPFSPDGKPCTPPALNCYWPLNDYGFYTTTGI-GYQPYR VVVLSFELLNAPATVCGPKLSTD-LIKNQCVNF (SEQ ID NO:2). In some embodiments, the target amino acid sequence used to generate the first ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 2.

An exemplary amino acid sequence to use to generate a first ISV domain directed to MERS-CoV spike protein may comprise the amino acid sequence: EAKPSGSVVEQAE-GVECDFSPLLSGTPPQVYNFKRLVFTNCNYNLTKLL-SLFSVNDFTCSQISP AAIASNCYSSLILDYFSY-PLSMKSDLSVSSAGPISQFNYKQSFSNPT-CLILATVPHNLTTITKPLKY SYINKCSRFLSDDRTE-VPQLVNANQYSPCVSIVPSTVWEDGDYYRKQLS-PLEGGGWLVASGS TVAMTE-QLQMGFGITVQYGTDTNSVCPKLEFANDTKI-ASQLGNCVEY (SEQ ID NO:3). In some embodiments, the target amino acid sequence used to generate the first ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 3.

An exemplary amino acid sequence to use to generate a first ISV domain directed to Influenza A (strain H1N1) hemagglutinin may comprise the amino acid sequence: DTICIGYHANNSTDTVDTVLEKNVTVTHSVNLLED-SHNGKLCRLKGIAPLQLGKCNIAGWLLGNP ECDPLLPVRSWSYIVETPNSENGICYPGDFIDYEEL-REQLSSVSSFERFEIFPKESSWPNHNTN GVTAACSHEGKSSFYRNLLWLTEKEGSYPKLKN-SYVNKKGKEVLVLWGIHHPPNSKEQQNLY QNENAY-VSVVTSNYNRRFTPEIAERPKVRDQAGRM-NYYWTLLKPGDTIIFEANGNLIAPMYAFA LSRGFGSGIITSNASMHECNTKCQTPLGAIN-SSLPYQNIHPVTIGECPKYVRSAKLRMVTGLRNI PSIQSRGLFGAIAGFIEGGWTGMIDGWYGYHHQ-NEQGSGYAADQKSTQNAINGITNKVNTVIE KMNIQFTAVGKEFNKLEKR-MENLNKKVDDGFLDIWTYNAELLVLLEN-ERTLDFHDSNVKNLYEK VKSQLKNNA-KEIGNGCFEFYHKCDNECMESVRNGTYDYPKY-SEESKLNREKVDGVKLESMGI YQ (SEQ ID NO: 4). In some embodiments, the target amino acid sequence used to generate the first ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 4.

An exemplary amino acid sequence to use to generate a first ISV domain directed to Influenza A (strain H3N2) hemagglutinin may comprise the amino acid sequence: QDLPGNDNN-STATLCLGHHAVPNGTLVKTITNDQIEVT-NATELVQSSSTGKICNNPHRILDGINC TLIDALLGDPHCDGFQNEKWDLFVERSKAFSNCY-PYDVPDYASLRSLVASSGTLEFINEGFNW TGVTQNGGSSACKRGPDSGFFSRLNWLYKSG-STYPVQNVTMPNNDNSDKLYIWGVHHPSTD KEQTNLYVQASGKVTVSTKRSQQTIIPNVGSRPWVR-GLSSRISIYWTIVKPGDILVINSNGNLIAP RGYFKMRTGKSSIMRSDAPIGTCSSECITPNG-SIPNDKPFQNVNKITYGACPKYVKQNTLKLAT GMRNVPEKQTRGIFGAIAGFIENGWEGMIDGWYG-FRHQNSEGTGQAADLKSTQAAIDQINGKL NRVIEKT-NEKFHQIEKEFSEVEGRIQDLEKYVEDTKIDLWSYN-AELLVALENQHTIDLTDSEMNK LFEKTRRQLRENAEDMGNGCFKIYHKCDNACIG-SIRNGTYDHDVYRDEALNNRFQIKGVELKS GYKDW (SEQ ID NO: 5). In some embodiments, the target amino acid sequence used to generate the first ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 5.

In order to generate a second ISV domain a target antigen is required. The amino acid sequence of target antigens that find use in the present disclosure include without limitation, the sequence to human MUC2, human MUC5AC, human MUC5B, human MUC1, human MUC4, human MUC11, mouse MUC2, mouse MUC5AC, mouse MUC5B, mouse MUC1, mouse MUC4, mouse MUC11, hamster MUC2, hamster MUC5AC, hamster MUC5B, hamster MUC1, hamster MUC4, hamster MUC11, etc. An exemplary amino acid sequence to use to generate a second ISV domain directed to human MUC5AC may comprise the amino acid sequence: WTKWFDVDFPSPGPHGGDKETYNNIIRSGEKI-CRRPEEITRLQCRAESHPEVNIEHLGQVVQC SREEGLVCRNQDQQGPFKMCLNYEVRVLC (SEQ ID NO: 6). In some embodiments, the target amino acid sequence used to generate the second ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 6.

An exemplary amino acid sequence to use to generate a second ISV domain directed to mouse MUC5AC may comprise the amino acid sequence: WTKWFDTDFPVPGPHGGDLETYSNIERSGERL-CHREEITQLQCRAKNYPEREMEDLGQVVKC DPSVGLVCNNRDQGGDSGMCLNYEVRLLC (SEQ ID NO: 7). In some embodiments, the target amino acid sequence used to generate the second ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 7.

An exemplary amino acid sequence to use to generate a second ISV domain directed to hamster MUC5AC may comprise the amino acid sequence: NWTDWID-GSYPGPDRNSGDFDTFANLRSKGYKFCEKPQNVE-CRAQFFPNTPLEELGQDVTC NRDEGLICLNKNQLP-PICYNYEIRIECCTIVDTCSTASTTTHPTSHEVSTET-KTTWTTSSHSSSSK DTSTLSATIHTRNRATD-SPHTISTPVTTHCQPQCTWTQWFDTDFPVPGPHGG-DLEDTSGMCLN YEVRVLC (SEQ ID NO: 8). In some embodiments, the target amino acid sequence used to generate the second ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 8.

An exemplary amino acid sequence to use to generate a second ISV domain directed to human MUC5B may comprise the amino acid sequence: WSEWL-DYSYPMPGPSGGDFDTYSNIRAAGGAVCEQPLGLE-CRAQAQPGVPLGELGQVVECS LDFGLVCRNREQVGKFKMCFNYEIRVFC (SEQ ID NO: 9). In some embodiments, the target amino acid sequence used to generate the second ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 9.

An exemplary amino acid sequence to use to generate a second ISV domain directed to mouse MUC5B may comprise the amino acid sequence: WTEWF-DADYPNPGPRGGDFEVYAVFREVGYIFCDQPKDIE-CRSEKEPDRPLETLEQVVQCDV RFGLICKNINQSGPLQYCDNYHVRLLC (SEQ ID NO: 10). In some embodiments, the target amino acid sequence used to generate the target amino acid sequence used to generate the second ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 10.

In some embodiments, a specific region of a mucin may be used to generate the second ISV domain. Suitable regions and/or domains for the generation of second ISV domains include without limitation, a MUC2 protein WxxW repeating region, cysteine rich domains, non-repetitive regions, etc.

In some embodiments, the amino acid sequence of the first ISV domain may comprise the amino acid sequence: QVQLQESGGGLVQAGGSLRLS-CAASGTIFQVGSMGWYRQAPGKEREFVA-TIADGSSTNYADS VKGRFTISRD-NAKNTVYLQMNSLKPEDTAVYYCAALGQVSEYNS-ASYEWTYPYWGQGTQVTV SS (SEQ ID NO: 11). In some embodiments, the amino acid sequence of the first ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 11. In some embodiments, the CDR sequences found within the first ISV domain are GTIFQVGSM (CDR1; SEQ ID NO: 12), EFVA-TIADGSSTNY (CDR2; SEQ ID NO: 13) and AALGQV-SEYNSASYEWTYPY (CDR3; SEQ ID NO: 14). In some embodiments, the amino acid sequence of the CDR sequences of the first ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 12, 13, or 14.

In some embodiments, the amino acid sequence of the first ISV domain may comprise the amino acid sequence: QVQLQESGGGLVQAGGSLRLSCAASG-NIFNEYFMGWYRQAPGKEREFVATIDQGANTYYADS VKGRFTISRDNAKNTVYLQMNSLKPEDTAVYYCAV-IGSDVYGHAYWGQGTQVTVSS (SEQ ID NO: 15). In some embodiments, the amino acid sequence of the first ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 15. In some embodiments, the CDR sequences found within the first ISV domain are GNIFNEYFM (CDR1; SEQ ID NO: 16), EFVATIDQGAN-TYY (CDR2; SEQ ID NO: 17) and AVIGSDVYGHAY (CDR3; SEQ ID NO: 18). In some embodiments, the amino acid sequence of the CDR sequences of the first ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 16, 17, or 18.

In some embodiments, the amino acid sequence of the first ISV domain may comprise the amino acid sequence: QVQLQESGGGLVQAGGSLRLS-CAASGTIFQVGSMGWYRQAPGKEREFVA-TIADGSSTNYADS VKGRFTISRD-NAKNTVYLQMNSLKPEDTAVYYCAALGQVSE-YNSASYEWTYPYWGQGTQVTV SS (SEQ ID NO: 19). In some embodiments, the amino acid sequence of the first ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 19. In some embodiments, the CDR sequences found within the first ISV domain are GTIFQVGSM (CDR1; SEQ ID NO: 20), EFVA-TIADGSSTNY (CDR2; SEQ ID NO: 21) and AALGQV- SEYNSASYEWTYPY (CDR3; SEQ ID NO: 22). In some embodiments, the amino acid sequence of the CDR sequences of the first ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 20, 21, or 22.

In some embodiments, the amino acid sequence of the first ISV domain may comprise the amino acid sequence: QVQLQESGGGLVQAGGSLRLSCAASGSIFGIV-VMGWYRQAPGKEREFVASINWGANTYYADS VKGRFTISRDNAKNTVYLQMNSLKPEDTAVYY-CAAHWHYDYPYDRDFLYWGQGTQVTVSS (SEQ ID NO: 23). In some embodiments, the amino acid sequence of the first ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 23. In some embodiments, the CDR sequences found within the first ISV domain are GSIFGIVVM (CDR1; SEQ ID NO: 24), EFVASINWGANTYY (CDR2; SEQ ID NO: 25) and AAHWHYDYPYDRDFLY (CDR3; SEQ ID NO: 26). In some embodiments, the amino acid sequence of the CDR sequences of the first ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 24, 25, or 26.

In some embodiments, the amino acid sequence of the first ISV domain may comprise the amino acid sequence: QVQLQESGGGLVQAGGSLRLSCAASGTI-FYTRDMGWYRQAPGKERELVAAITAGANTYYADS VKGRFTISRDNAKNTVYLQMNSLKPEDTAVYY-CAAYPNAPDISDEDYNEGYLYWGQGTQVTVS S (SEQ ID NO: 27). In some embodiments, the amino acid sequence of the first ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 27. In some embodiments, the CDR sequences found within the first ISV domain are GTIFYTRDM (CDR1; SEQ ID NO: 28), ELVAAITAGANTYY (CDR2; SEQ ID NO: 29) and AAY-PNAPDISDEDYNEGYLY (CDR3; SEQ ID NO: 30). In some embodiments, the amino acid sequence of the CDR sequences of the first ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 28, 29, or 30.

In some embodiments, the amino acid sequence of the first ISV domain may comprise the amino acid sequence: QVQLQESGGGLVQAGGSLRLS-CAASGTIFSWKTMGWYRQAPGKEREFVAS-INGGTNTNYAD SVKGRFTISRD-NAKNTVYLQMNSLKPEDTAVYYCAASRPNIPFR-ADYYDQRHTYWGQGTQVT VSS (SEQ ID NO: 31). In some embodiments, the amino acid sequence of the first ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 31. In some embodiments, the CDR sequences found within the first ISV domain are GTIFSWKTM (CDR1; SEQ ID NO: 32), EFVAS-INGGTNTNY (CDR2; SEQ ID NO: 33) and AASRPNIP-FRADYYDQRHTY (CDR3; SEQ ID NO: 34). In some embodiments, the amino acid sequence of the CDR sequences of the first ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 32, 33, or 34.

In some embodiments, the amino acid sequence of the first ISV domain may comprise the amino acid sequence: QVQLQESGGGLVQAGGSLRLSCAASGSIS-RDYDMGWYRQAPGKEREFVAGINVGGTTNYAD SVKGRFTISRDNAKNTVYLQMNSLKPEDTAVYY-CAVHAVYTDGWEDGYLYPLPYWGQGTQVT VSS (SEQ ID NO: 35). In some embodiments, the amino acid sequence of the first ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 35. In some embodiments, the CDR sequences found within the first ISV domain are GSISRDYDM (CDR1; SEQ ID NO: 36), EFVAGINVGGTTNY (CDR2; SEQ ID NO: 37) and AVHAVYTDGWEDGYLYPLPY (CDR3; SEQ ID NO: 38). In some embodiments, the amino acid sequence of the CDR sequences of the first ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 36, 37, or 38.

In some embodiments, the amino acid sequence of the first ISV domain may comprise the amino acid sequence: QVQLQESGGGLVQAGGSLRLSCAASGTISYT-PIMGWYRQAPGKEREFVATIALGTTTNYADSV KGRFTISRDNAKNTVYLQMNSLKPEDTAVYY-CAVVSFATTRYDPVFTDTLPYWGQGTQVTVSS (SEQ ID NO: 39). In some embodiments, the amino acid sequence of the first ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 39. In some embodiments, the CDR sequences found within the first ISV domain are GTISYTPIM (CDR1; SEQ ID NO: 40), EFVA-TIALGTTTNY (CDR2; SEQ ID NO: 41) and AVVSFATT-RYDPVFTDTLPY (CDR3; SEQ ID NO: 42). In some embodiments, the amino acid sequence of the CDR sequences of the first ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 40, 41, or 42.

In some embodiments, the amino acid sequence of the first ISV domain may comprise the amino acid sequence: QVQLQESGGGLVQAGGSLRLS-CAASGTIFQVSSMGWYRQAPGKERKFVA-TIADGSSTNYAGS VKGRFTISRD-NAKNTVYLQMNSLKPEDTAVYYCAALGQ-VSEYNSASYEWTYPYWGQGTQVTV SS (SEQ ID NO: 43). In some embodiments, the amino acid sequence of the first ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 43. In some embodiments, the CDR sequences found within the first ISV domain are GTIFQVSSM (CDR1; SEQ ID NO: 44), KFVA-TIADGSSTNY (CDR2; SEQ ID NO: 45) and AALGQV-SEYNSASYEWTYPY (CDR3; SEQ ID NO: 46). In some embodiments, the amino acid sequence of the CDR sequences of the first ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 44, 45, or 46.

In some embodiments, the amino acid sequence of the first ISV domain may comprise the amino acid sequence: QVQLQESGGGLVQAGGSLRLSCAASGSIS-RDYDMGWYRQAPGKERKFVAGINVGGTTNYAG SVKGRFTISRDNAKNTVYLQMNSLKPEDTAVYY-CAVHAVYTDGWEDGYLYPLPYWGQGTQVT VSS (SEQ ID NO: 47). In some embodiments, the amino acid sequence of the first ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 47. In some embodiments, the CDR sequences found within the first ISV domain are GSISRDYDM (CDR1; SEQ ID NO: 48), KFVAGINVGGTTNY (CDR2; SEQ ID NO: 49) and AVHAVYTDGWEDGYLYPLPY (CDR3; SEQ ID NO: 50). In some embodiments, the amino acid sequence of the CDR sequences of the first ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 48, 49, or 50.

In some embodiments, the amino acid sequence of the first ISV domain may comprise the amino acid sequence: QVQLQESGGGLVQAGGSLRLSCAASGTISYT-PIMGWYRQAPGKERKFVATIALGTTTNYAGSV KGRFTISRDNAKNTVYLQMNSLKPEDTAVYY-CAVVSFATTRYDPVFTDTLPYWGQGTQVTVSS (SEQ ID NO: 51). In some embodiments, the amino acid sequence of the first ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 51. In some embodiments, the CDR sequences found within the first ISV domain are GTISYTPIM (CDR1; SEQ ID NO: 52), KFVA-TIALGTTTNY (CDR2; SEQ ID NO: 53) and AVVSFATT-RYDPVFTDTLPY (CDR3; SEQ ID NO: 54). In some embodiments, the amino acid sequence of the CDR sequences of the first ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 52, 53, or 54.

In some embodiments, the amino acid sequence of the second ISV domain may comprise the amino acid sequence: QVQLQESGGGLVQAGGSLRLSCAASGNI-SYYRHMGWYRQAPGKERELVASIGDGGNTNYAD SVKGRFTISRDNAKNTVYLQMNSLKPEDTAVYY-CAVVHNTYLLYDPYVWDYLLLYWGQGTQVT VSS (SEQ ID NO: 55). In some embodiments, the amino acid sequence of the second ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 55. In some embodiments, the CDR sequences found within the second ISV domain are GNISYYRHM (CDR1; SEQ ID NO: 56), ELVASIGDGGNTNY (CDR2; SEQ ID NO: 57) and AVVHNTYLLYDPYVWDYLLLY (CDR3; SEQ ID NO: 58). In some embodiments, the amino acid sequence of the CDR sequences of the second ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 56, 57, or 58.

In some embodiments, the amino acid sequence of the second ISV domain may comprise the amino acid sequence: QVQLQESGGGLVQAGGSLRLSCAASGNI-SYDWYMGWYRQAPGKEREFVASINRGATTNYAD SVKGRFTISRDNAKNTVYLQMNSLKPEDTAVYY-CAVDDYSDDWYGYWGQGTQVTVSS (SEQ ID NO: 59). In some embodiments, the amino acid sequence of the second ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 59. In some embodiments, the CDR sequences found within the second ISV domain are GNISYDWYM (CDR1; SEQ ID NO: 60), EFVASINRGATTNY (CDR2; SEQ ID NO: 61) and AVD-DYSDDWYGY (CDR3; SEQ ID NO: 62). In some embodiments, the amino acid sequence of the CDR sequences of the second ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 60, 61, or 62.

In some embodiments, the amino acid sequence of the second ISV domain may comprise the amino acid sequence: QVQLQESGGGLVQAGGSLRLSCAASGNI-SYYRRMGWYRQAPGKERELVASIGDGGNTNYAD SVKGRFTISRDNAKNTVYLQMNSLKPEDTAVYY-CAVVRKTYLLYDPYVWYYVLLYWGQGTQVT VSS (SEQ ID NO: 63). In some embodiments, the amino acid sequence of the second ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 63. In some embodiments, the CDR sequences found within the second ISV domain are GNISYYRRM (CDR1; SEQ ID NO: 64), ELVASIGDGGNTNY (CDR2; SEQ ID NO: 65) and AVVRKTYLLYDPYVWYYVLLY (CDR3; SEQ ID NO: 66). In some embodiments, the amino acid sequence of the CDR sequences of the second ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 64, 65, or 66.

In some embodiments, the amino acid sequence of the second ISV domain may comprise the amino acid sequence: QVQLQESGGGLVQAGGSLRLSCAASGNISP-TYLMGWYRQAPGKEREFVAGIAHGASTNYADS VKGRFTISRDNAKNTVYLQMNSLKPEDTAVYY-CAVNPYALDVLVYWGQGTQVTVSS (SEQ ID NO: 67). In some embodiments, the amino acid sequence of the second ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 67. In some embodiments, the CDR sequences found within the second ISV domain are GNISPTYLM (CDR1; SEQ ID NO: 68), EFVAGIAHGASTNY (CDR2; SEQ ID NO: 69) and AVNPYALDVLVY (CDR3; SEQ ID NO: 70). In some embodiments, the amino acid sequence of the CDR sequences of the second ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 68, 69, or 70.

In some embodiments, the amino acid sequence of the second ISV domain may comprise the amino acid sequence: QVQLQESGGGLVQAGGSLRLSCAASGSIFLP-PYMGWYRQAPGKEREFVAGIGGGSSTYYADS VKGRFTISRDNAKNTVYLQMNSLKPEDTAVYYCAV-VYYTDPSDEFAHYYWGQGTQVTVSS (SEQ ID NO: 71). In some embodiments, the amino acid sequence of the second ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 71. In some embodiments, the CDR sequences found within the second ISV domain are GSIFLPPYM (CDR1; SEQ ID NO: 72), EFVAGIGGGSSTYY (CDR2; SEQ ID NO: 73) and AVVYYTDPSDEFAHYY (CDR3; SEQ ID NO: 74). In some embodiments, the amino acid sequence of the CDR sequences of the second ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 72, 73, or 74.

In some embodiments, the amino acid sequence of the second ISV domain may comprise the amino acid sequence: QVQLQESGGGLVQAGGSLRLSCAASGTIS-RYIYMGWYRQAPGKEREFVASIARGTITYYADSV KGRFTISRDNAKNTVYLQMNSLKPEDTAVYY-CAADNKYEDAYYGYWGQGTQVTVSS (SEQ ID NO: 75). In some embodiments, the amino acid sequence of the second ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 75. In some embodiments, the CDR sequences found within the second ISV domain are GTISRYIYM (CDR1; SEQ ID NO: 76), EFVASIARGTITYY (CDR2; SEQ ID NO: 77) and AADNKYEDAYYGY (CDR3; SEQ ID NO: 78). In some embodiments, the amino acid sequence of the CDR sequences of the second ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 76, 77, or 78.

In some embodiments, the amino acid sequence of the second ISV domain may comprise the amino acid sequence: QVQLQESGGGLVQAGGSLRLSCAASGNIS-PTNLMGWYRQAPGKEREFVAAIAHGASTNYADS VKGRFTISRDNAKNTVYLQMNSLKPED-TAVYYCVVNPYALDVLVYWGQGTQVTVSS (SEQ ID NO: 79). In some embodiments, the amino acid sequence of the second ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 79. In some embodiments, the CDR sequences found within the second ISV domain are GNISPTNLM (CDR1; SEQ ID NO: 80), EFVAAIAHGASTNY (CDR2; SEQ ID NO: 81) and VVNPYALDVLVY (CDR3; SEQ ID NO: 82). In some embodiments, the amino acid sequence of the CDR sequences of the second ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 80, 81, or 82.

In some embodiments, the amino acid sequence of the second ISV domain may comprise the amino acid sequence: QVQLQESGGGLVQAGGSLRLSCAASGTISYT-PIMGWYRQAPGKEREFVAAIAHGASTNYADS VKGRFTISRDNAKNTVYLQMNSLKPEDTAVYY-CAVNPYALDVLVYWGQGTQVTVSS (SEQ ID NO: 83). In some embodiments, the amino acid sequence of the second ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 83. In some embodiments, the CDR sequences found within the second ISV domain are GTISYTPIM (CDR1; SEQ ID NO: 84), EFVAAIAHGASTNY (CDR2; SEQ ID NO: 85) and AVNPYALDVLVY (CDR3; SEQ ID NO: 86). In some embodiments, the amino acid sequence of the CDR sequences of the second ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 84, 85, or 86.

In some embodiments, the amino acid sequence of the second ISV domain may comprise the amino acid sequence: QVQLQESGGGLVQAGGSLRLSCAASGNISPEY-RMGWYRQAPGKEREFVAGIDYGGNTYYAD SVKGRFTISRDNAKNTVYLQMNSLKPEDTAVYY-CAVRTYDGGTHTYWGQGTQVTVSS (SEQ ID NO: 87). In some embodiments, the amino acid sequence of the second ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 87. In some embodiments, the CDR sequences found within the second ISV domain are GNISPEYRM (CDR1; SEQ ID NO: 88), EFVAGIDYGGNTYY (CDR2; SEQ ID NO: 89) and AVR-TYDGGTHTY (CDR3; SEQ ID NO: 90). In some embodiments, the amino acid sequence of the CDR sequences of the second ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 88, 89, or 90.

In some embodiments, the amino acid sequence of the second ISV domain may comprise the amino acid sequence: QVQLQESGGGLVQAGGSLRLSCAASGNISP-TYLMGWYRQAPGKEREFVAGIAHGASTNYADS VKGRFTISRDNAKNTVYLQMNSLKPEDTAVYY-CAVNPYALDVLVYWGQGTQVTVSS (SEQ ID NO: 91). In some embodiments, the amino acid sequence of the second ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 91. In some embodiments, the CDR sequences found within the second ISV domain are GNISPTYLM (CDR1; SEQ ID NO: 92), EFVAGIAHGASTNY (CDR2; SEQ ID NO: 93) and AVNPYALDVLVY (CDR3; SEQ ID NO: 94). In some embodiments, the amino acid sequence of the CDR sequences of the second ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 92, 93, or 94.

In some embodiments, the amino acid sequence of the second ISV domain may comprise the amino acid sequence: QVQLQESGGGLVQAGGSLRLSCAASGNI-FYIPVMGWYRQAPGKEREFVAAIAYGTTTNYADSV KGRFTISRDNAKNTVYLQMNSLKPEDTAVYY-CAVAYYTYWGQGTQVTVSS (SEQ ID NO: 95). In some embodiments, the amino acid sequence of the second ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 95. In some embodiments, the CDR sequences found within the second ISV domain are GNIFYIPVM (CDR1; SEQ ID NO: 96), EFVAA-IAYGTTTNY (CDR2; SEQ ID NO: 97) and AVAYYTY (CDR3; SEQ ID NO: 98). In some embodiments, the amino acid sequence of the CDR sequences of the second ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 96, 97, or 98.

In some embodiments, the amino acid sequence of the second ISV domain may comprise the amino acid sequence: QVQLQESGGGLVQAGGSLRLS-CAASGTISPAPIMGWYRQAPGKEREFVAAINHGAI TYYADSVKGRFTISRDNAKNTVYLQMNSLKPED-TAVYYCAVYPHSYWGQGTQVTVSS (SEQ ID NO: 99). In some embodiments, the amino acid sequence of the second ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 99. In some embodiments, the CDR sequences found within the second ISV domain are GTISPAPIM (CDR1; SEQ ID NO: 100), EFVAAINHGAITYY (CDR2; SEQ ID NO: 101) and AVYPHSY (CDR3; SEQ ID NO: 102). In some embodiments, the amino acid sequence of the CDR sequences of the second ISV domain has at least 60%, at least 65%, at least 70%, at least 75%, at least 80%, at least 85%, at least 90%, at least 95%, at least 98%, at least 99%, or 100%, amino acid sequence identity with that of SEQ ID NO: 100, 101, or 102.

In some embodiments, a multispecific protein is used in place of a bispecific protein. In some embodiments, the multispecific protein comprises two or more ISVs that specifically bind to a protein expressed on the surface of an airborne infectious virus; and one or more ISVs that specifically binds to a mucin present on ocular, nasopharyngeal, tracheal and/or oral surfaces of a mammal; joined by a polypeptide linker. Multispecific proteins differ from bispecific proteins in that multispecific proteins comprise three or more ISVs, e.g. two or more ISVs that specifically bind to a protein expressed on the surface of an airborne infectious virus; and one or more ISVs that specifically binds to a mucin.

Kits

Also provided are kits for use in the methods. The agents of a kit can be present in the same or separate containers. The agents may also be present in the same container. In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), flash drive, and the like, on which the information has been recorded. Yet another form of these instructions that may be present is a website address which may be used via the internet to access the information at a removed site.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

Examples

ISV Screening and Production

For ISV screening, flag tagged antigen (corresponding to SEQ ID NO: 1, 6, 7, or 8) was incubated with induced yeast library, then stained with AF647 conjugated anti-flag antibody and sorted for AF647 positive yeast by magnetic-activated cell sorting (MACS) or fluorescence-activated cell sorting (FACS). After several rounds of selection, antigen binding yeast were enriched to above 20% of the total population. 48-96 antigen binding clones were sequenced to identify nanobody sequences that bound antigen. ISV were expressed in *E. coli* and purified using Ni-NTA beads. For bispecific ISV, nanobody against an airborne virus and nanobody against mucin were joined by GS linker.

TABLE 1

Targeted virus and mucin for bispecific ISV generation.
The mucus-tethering bispecific ISV can be generated to
prevent against various airborne infectious virus including
but not limited to SARS-CoV-2, SARS-CoV, MERS-CoV and
influenza A virus. The surface glycoproteins targeted
to generate virus neutralizing ISV are spike proteins
or hemagglutinins. The mucins targeted to generate mucus-
tethering ISV are gel-forming mucins MUC2, MUC5AC and MUC5B,
as well as membrane mucins MUC1, MUC4 and MUC11.

| Nanobody target | Target Species | Target Protein |
|---|---|---|
| Virus | Severe acute respiratory syndrome coronavirus (SARS-CoV-2) | Spike protein |
| | Severe acute respiratory syndrome coronavirus (SARS-CoV) | Spike protein |
| | Middle East respiratory syndrome coronavirus (MERS-CoV) | Spike protein |
| | Influenza A virus | Hemagglutinin |
| Mucins | *Homo Sapiens* (human) | MUC2, MUC5AC, MUC5B, MUC1, MUC4, MUC11 |
| | *Mus musculus* (house mouse) | MUC2, MUC5AC, MUC5B, MUC1, MUC4, MUC11 |
| | *Mesocricetus auratus* (golden hamster) | MUC2, MUC5AC, MUC5B, MUC1, MUC4, MUC11 |

Validation of SARS-CoV-2 Neutralizing ISV.

SARS-CoV-2 pseudovirus and human ACE2 (hACE2) overexpressed HEK-293T cells were used to analysis neutralizing effect of candidate ISV. An HIV-based lentiviral system was used to produce viral particles pseudotyped with SARS-CoV-2 Spike protein. Pseudovirus was diluted in culture medium to obtain 10% infection ratio and incubated with ISV (R2, R3, R13, R14, R15, R17, R18, R19 corresponding to SEQ ID NO: 11, 15, 19, 23, 27, 31, 35, and 39) for 1 hour at 37° C. prior to addition to hACE2-293T cells. Upon infection cells express ZsGreen fluorescent protein. Images were captured 48 hours after infection. Flow cytometry analysis of infected cell were performed after imaging. Affinity maturation of nanobody R13 and R18 (corresponding to SEQ ID NO: 43 and 47) showed around 100 times increased neutralizing effect calculated by IC50.

Validation of MUC5AC Tethering ISV.

Mucus secreting cell line Calu-3 was used to validate mucus-tethering ISV. Sections of Calu-3 cells in transwells were stained with a MUC5AC antibody (Alexa Fluor 647 conjugated) or indicated ISV (Alexa Fluor 647 conjugated control nanobody, M2, M16 and M17; M2, M16 and M17 correspond to SEQ ID NO: 55, 63 and 67). Cells were stained with DAPI (blue) which stain nucleus, a MUC5AC antibody (red), a major mucin in the mucus layer. The presence of the nanobody M17 in calu-3 condition media and human nasal mucus samples was validated using Western blot analysis.

Validation of Mucus-Tethering Bispecific ISV.

Sections of Calu-3 cells in transwell were stained with mucus-tethering ISV M17 (SEQ ID NO: 67) and its bispecific version joined with anti-SARS-CoV-2 ISV (R13, R17 and R19; SEQ ID NO:19, 31 and 39, respectively). M22 (SEQ ID NO: 75) was used as a negative control nanobody with poor affinity to mucin. For neutralization assays, hACE2-293T cells were coated in mucus harvested from Calu-3 cells. The bispecific protein comprising the ISV R19M17 showed higher inhibitory effects over virus specific nanobody R19 and its bispecific version jointed with a non-mucus-tethering nanobody M22 (R19M22).

Validation of Hamster and Mouse Mucus-Tethering ISV.

Golden hamster trachea sections were stained with anti-MUC5AC antibody (Alexa Fluor 647 conjugated) and nanobody candidates Ham2 and Ham28 (Alexa Fluor 647 conjugated; corresponding to SEQ ID NO: 87 and 91). Mouse trachea sections were stained with nanobody candidates Mus4 and Mus6 (Alexa Fluor 647 conjugated; corresponding to SEQ ID NO: 95 and 99). Nuclei were stained with DAPI (blue) and MUC5AC was stained with a MUC5AC antibody (red).

---

What is claimed is:

1. A bispecific protein comprising:
a first immunoglobulin single variable domain (ISV) that specifically binds to a protein expressed on the surface of an airborne infectious virus; and a second ISV that specifically binds to a mucin present on ocular, nasopharyngeal, tracheal and/or oral surfaces of a mammal; joined by a polypeptide linker.

2. The bispecific protein of claim 1, wherein the first ISV specifically binds to a conserved domain in the spike envelope protein encoded by an airborne infectious virus selected from a SARS-CoV-2, a SARS-COV-1, or a MERS-COV.

3. The bispecific protein of claim 1, wherein the second ISV specifically binds to a human mucin protein selected from a human MUC5AC, human MUC5B, human MUC1, human MUC4, or human MUC11.

4. The bispecific protein of claim 1, wherein the first ISV comprises a variable heavy homodimer (VHH) domain with the amino acid sequence of any of SEQ ID NO: 11; SEQ ID NO: 15; SEQ ID NO: 19; SEQ ID NO:23; SEQ ID NO:27; SEQ ID NO:31; SEQ ID NO:35; SEQ ID NO:39; SEQ ID NO: 43; SEQ ID NO:47; SEQ ID NO:51; or an ISV having the CDR1, CDR2 and CDR3 sequences of SEQ ID NO:11; SEQ ID NO:15; SEQ ID NO:19; SEQ ID NO:23; SEQ ID NO:27; SEQ ID NO:31; SEQ ID NO:35; SEQ ID NO:39; SEQ ID NO:43; SEQ ID NO:47; SEQ ID NO:51.

5. The bispecific protein of claim 1, wherein the second ISV comprises a variable heavy homodimer (VHH) domain having the amino acid sequence of any of SEQ ID NO:55; SEQ ID NO:59; SEQ ID NO:63; SEQ ID NO:67; SEQ ID NO:71; SEQ ID NO:75; SEQ ID NO: 79; SEQ ID NO:83; or an ISV having the CDR1, CDR2 and CDR3 sequences of any of SEQ ID NO: 55; SEQ ID NO:59; SEQ ID NO:63; SEQ ID NO:67; SEQ ID NO:71; SEQ ID NO:75; SEQ ID NO:79; SEQ ID NO:83.

6. The bispecific protein of claim 1, wherein the polypeptide linker is from 8 to 30 amino acids in length.

7. The bispecific protein of claim 6, wherein the linker comprises a poly-(gly-ser) sequence.

8. The bispecific protein of claim 1, wherein one or both of the ISV are VHH domains.

9. A pharmaceutical formulation comprising the bispecific protein of claim 1.

10. The formulation of claim 9, wherein the formulation is an aerosol formulation.

11. A method of reducing infection of an individual during exposure to an airborne infectious respiratory virus, the method comprising contacting mucosal surfaces with an effective dose of a pharmaceutical composition according to claim 9.

12. The method of claim 11, wherein the mucosal surface is an ocular, nasopharyngeal, tracheal and/or oral surface of a mammal.

13. The method of claim 12, wherein the airborne infectious respiratory virus is SARS-CoV; SARS-COV2, MERS-COV; or influenza virus.

14. The method of claim 13, wherein the mucosal surface comprises one or more of human MUC2, human MUC5AC, human MUC5B, human MUC1, human MUC4, and human MUC11.

15. A method of tethering an airborne infectious respiratory virus to a mucosal surface for inactivation, the method comprising:
coating a mucosal surface with a pharmaceutical composition according to claim 9 at a dose effective to reduce infectivity of the airborne infectious virus when the virus contacts the mucosal surface.

16. The method of claim 15, wherein the mucosal surface is an ocular, nasopharyngeal, tracheal and/or oral surface of a mammal.

17. The method of claim 16, wherein the airborne infectious respiratory virus is SARS-CoV; SARS-COV2, MERS-COV; or influenza virus.

18. The method of claim 17, wherein the mucosal surface comprises one or more of human MUC2, human MUC5AC, human MUC5B, human MUC1, human MUC4, and human MUC11.

19. A multispecific protein comprising:
two or more ISVs that specifically bind to a protein expressed on the surface of an airborne infectious virus; and one or more ISVs that specifically binds to a mucin present on ocular, nasopharyngeal, tracheal and/or oral surfaces of a mammal; joined by a polypeptide linker.

20. The multi-specific protein of claim 19, wherein the two or more ISVs that specifically bind to a protein expressed on the surface of an airborne infectious virus comprises a variable heavy homodimer (VHH) domain with the amino acid sequence of any of SEQ ID NO:11; SEQ ID NO: 15; SEQ ID NO:19; SEQ ID NO:23; SEQ ID NO:27; SEQ ID NO:31; SEQ ID NO:35; SEQ ID NO: 39; SEQ ID NO:43; SEQ ID NO:47; SEQ ID NO:51; or an ISV having the CDR1, CDR2 and CDR3 sequences of SEQ ID NO:11; SEQ ID NO:15; SEQ ID NO:19; SEQ ID NO:23; SEQ ID NO:27; SEQ ID NO: 31; SEQ ID NO:35; SEQ ID NO:39; SEQ ID NO:43; SEQ ID NO:47; SEQ ID NO:51 and wherein the one or more ISVs that specifically binds to a mucin present on ocular, nasopharyngeal, tracheal and/or oral surfaces of a mammal comprises a variable heavy homodimer (VHH) domain having the amino acid sequence of any of SEQ ID NO:55; SEQ ID NO:59; SEQ ID NO:63; SEQ ID NO:67; SEQ ID NO:71; SEQ ID NO: 75; SEQ ID NO:79; SEQ ID NO:83; or an ISV having the CDR1, CDR2 and CDR3 sequences of any of SEQ ID NO:55; SEQ ID NO:59; SEQ ID NO:63; SEQ ID NO:67; SEQ ID NO:71; SEQ ID NO:75; SEQ ID NO:79; SEQ ID NO:83.

* * * * *